(12) United States Patent
Choi et al.

(10) Patent No.: US 10,087,170 B2
(45) Date of Patent: Oct. 2, 2018

(54) COMPOUND, PHOTOSENSITIVE RESIN COMPOSITION INCLUDING THE SAME, AND COLOR FILTER

(71) Applicant: SAMSUNG SDI CO., LTD., Yongin-si, Gyeonggi-do (KR)

(72) Inventors: Eunjeong Choi, Suwon-si (KR);
Sohyun Kim, Suwon-si (KR);
Kyuyoung Kim, Suwon-si (KR);
Kwangwon Seo, Suwon-si (KR);
Young Lee, Suwon-si (KR);
Myoungyoup Shin, Suwon-si (KR);
Juho Jung, Suwon-si (KR); Gyuseok Han, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/691,950

(22) Filed: Aug. 31, 2017

(65) Prior Publication Data

US 2018/0072709 A1    Mar. 15, 2018

(30) Foreign Application Priority Data

Sep. 9, 2016  (KR) .......... 10-2016-0116731
Nov. 2, 2016  (KR) .......... 10-2016-0145180
May 8, 2017  (KR) .......... 10-2017-0057589

(51) Int. Cl.
*C07D 413/12* (2006.01)
*G02B 5/22* (2006.01)

(52) U.S. Cl.
CPC .......... *C07D 413/12* (2013.01); *G02B 5/223* (2013.01)

(58) Field of Classification Search
CPC .............. C07D 413/12; G02B 5/223
USPC ........................................ 549/394
See application file for complete search history.

(56) References Cited

U.S. PATENT DOCUMENTS 8,163,910 B2  4/2012  Lukhtanov
2014/0176653 A1*  6/2014  Fujie .............. C09D 11/328
  347/100

2014/0368573 A1*  12/2014  Fujie .............. C09B 11/24
  347/20
2017/0248845 A1*  8/2017  Kim .............. C07D 311/82
2017/0248846 A1*  8/2017  Kim .............. G03F 7/0163

FOREIGN PATENT DOCUMENTS

| JP | 09-157562 | * | 6/1997 |
| JP | 09-157562 | A | 6/1997 |
| JP | 2012-32754 | A | 2/2012 |
| JP | 2013-64099 | A | 4/2013 |
| JP | 2013-253168 | A | 12/2013 |
| JP | 5647279 | B2 | 12/2014 |
| JP | 2015-67815 | A | 4/2015 |
| JP | 2015-160939 | A | 9/2015 |
| JP | 5826071 | B2 | 12/2015 |
| JP | 2016-60828 | A | 4/2016 |
| JP | 2016-65220 | A | 4/2016 |
| KR | 10-2012-0002453 | A | 1/2012 |
| KR | 10-2015-0115719 | A | 10/2015 |
| TW | 201319050 | A | 5/2013 |
| TW | 201722926 | A | 7/2017 |
| WO | WO 2017/052169 | * | 3/2017 |

OTHER PUBLICATIONS

Search Report dated Mar. 21, 2018 for the corresponding Taiwanese Patent Application No. 106130560.

* cited by examiner

*Primary Examiner* — Daniel R Carcanague
(74) *Attorney, Agent, or Firm* — Lee & Morse, P.C.

(57) ABSTRACT

A compound, a photosensitive resin composition including the compound, and a color filter manufactured using the photosensitive resin composition, the compound being represented by Chemical Formula 1:

[Chemical Formula 1]

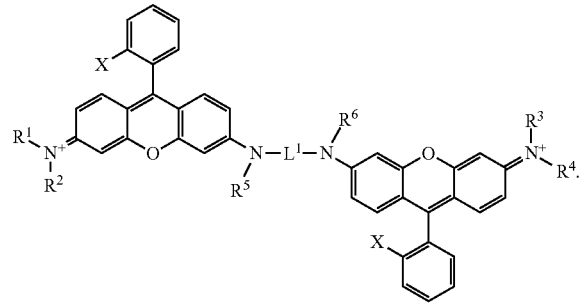

20 Claims, 2 Drawing Sheets

COMPOUND, PHOTOSENSITIVE RESIN COMPOSITION INCLUDING THE SAME, AND COLOR FILTER

CROSS-REFERENCE TO RELATED APPLICATION

Korean Patent Application Nos. 10-2016-0116731, 10-2016-0145180, and 10-2017-0057589 filed in the Korean Intellectual Property Office on Sep. 9, 2016, Nov. 2, 2016, and May 8, 2017, respectively, and entitled: "Novel Compound, Photosensitive Resin Composition Including the Same and Color Filter" is incorporated by reference herein in its entirety.

BACKGROUND

1. Field

Embodiments relate to a compound, a photosensitive resin composition including the same, and a color filter.

2. Description of the Related Art

A liquid crystal display device among many kinds of displays has an advantage of lightness, thinness, low cost, low power consumption for operation, and improved adherence to an integrated circuit and has been more widely used for a laptop computer, a monitor, and a TV screen. The liquid crystal display device includes a lower substrate on which a black matrix, a color filter, and an ITO pixel electrode are formed, and an upper substrate on which an active circuit portion including a liquid crystal layer, a thin film transistor, and a capacitor layer and an ITO pixel electrode are formed.

Color filters may be formed in a pixel region by sequentially stacking a plurality of color filters (e.g., may be formed of three primary colors such as red (R), green (G), and blue (B) in a predetermined order to form each pixel), and a black matrix layer is disposed in a predetermined pattern on a transparent substrate to form a boundary between the pixels.

SUMMARY

Embodiments are directed to a compound, a photosensitive resin composition including the same, and a color filter.

The embodiments may be realized by providing a compound represented by Chemical Formula 1:

[Chemical Formula 1]

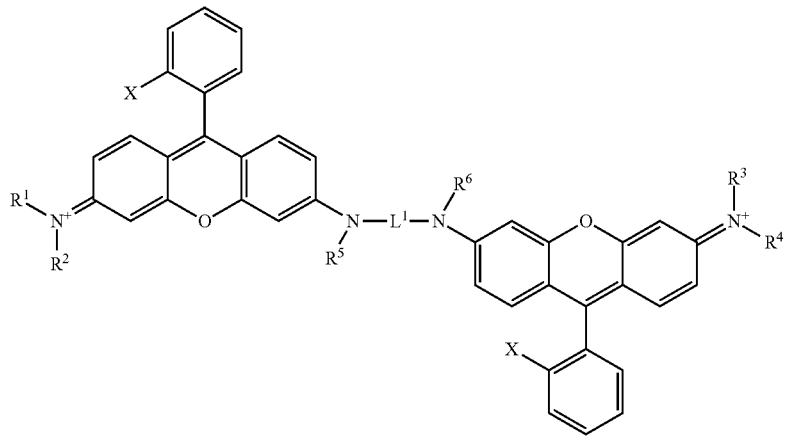

wherein, in Chemical Formula 1, $R^1$ to $R^6$ are each independently a hydrogen atom, a substituted or unsubstituted C1 to C20 alkyl group, or a substituted or unsubstituted C6 to C20 aryl group, $L^1$ is a substituted or unsubstituted C1 to C20 alkylene group, a substituted or unsubstituted C3 to C20 cycloalkylene group, a substituted or unsubstituted C6 to C20 arylene group, *—OC(=O)NH—*, *—O(C=O)—*, *—$NR^x$—*, or a combination thereof, in which $R^x$ is a substituted or unsubstituted C1 to C10 alkyl group, and X is a group represented by Chemical Formula X-1 or Chemical Formula X-2,

[Chemical Formula X-1]

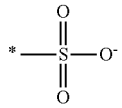

[Chemical Formula X-2]

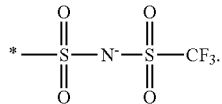

$L^1$ may be a group represented by Chemical Formula 2:

[Chemical Formula 2]

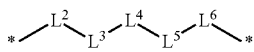

wherein, in Chemical Formula 2, $L^2$ to $L^6$ are each independently a single bond, a substituted or unsubstituted C1 to C10 alkylene group, a substituted or unsubstituted C3 to C20 cycloalkylene group, *—OC(=O)NH—*, *—O(C=O)—* or *—NR$^x$—*, in which R$^x$ is a substituted or unsubstituted C1 to C10 alkyl group, provided that all of $L^2$ to $L^6$ are not a single bond.

The group represented by Chemical Formula 2 may be a substituted or unsubstituted C1 to C20 alkylene group.

The group represented by Chemical Formula 2 may be a group represented by Chemical Formula 3:

[Chemical Formula 3]

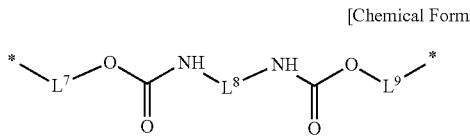

wherein, in Chemical Formula 3, $L^7$ to $L^9$ are each independently a substituted or unsubstituted C1 to C10 alkylene group, a substituted or unsubstituted C3 to C10 cycloalkylene group, or a combination thereof.

$L^7$ to $L^9$ may each independently be a substituted or unsubstituted C1 to C10 alkylene group or a group represented by Chemical Formula 3-1 or Chemical Formula 3-2:

[Chemical Formula 3-1]

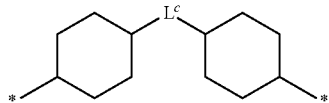

[Chemical Formula 3-2]

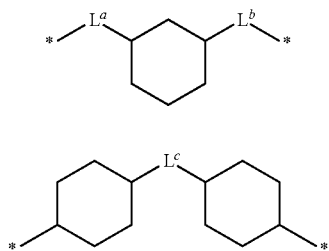

wherein, in Chemical Formula 3-1 and Chemical Formula 3-2, $L^a$ to $L^c$ are each independently a substituted or unsubstituted C1 to C5 alkylene group.

The group represented by Chemical Formula 2 may be a group represented by Chemical Formula 4:

[Chemical Formula 4]

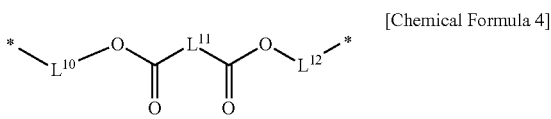

wherein, in Chemical Formula 4, $L^{10}$ to $L^{12}$ are each independently a substituted or unsubstituted C1 to C10 alkylene group.

The group represented by Chemical Formula 2 may be a group represented by Chemical Formula 5:

[Chemical Formula 5]

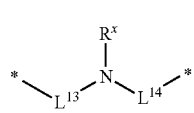

wherein, in Chemical Formula 5, $L^{13}$ and $L^{14}$ are each independently a substituted or unsubstituted C1 to C10 alkylene group, and R$^x$ is a substituted or unsubstituted C1 to C10 alkyl group.

At least one of $R^1$ to $R^4$ may be a group represented by Chemical Formula 6-1 or Chemical Formula 6-2:

[Chemical Formula 6-1]

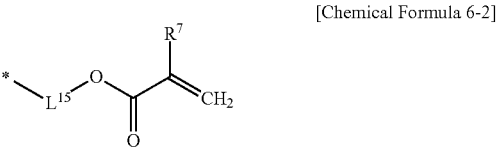

[Chemical Formula 6-2]

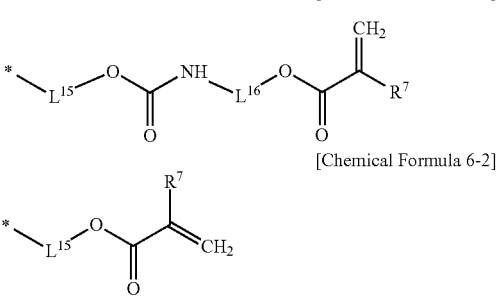

wherein, in Chemical Formula 6-1 and Chemical Formula 6-2, $R^7$ is a hydrogen atom or a substituted or unsubstituted C1 to C10 alkyl group, and $L^{15}$ and $L^{16}$ are each independently a substituted or unsubstituted C1 to C10 alkylene group.

The compound represented by Chemical Formula 1 may be represented by one of Chemical Formula 7 to Chemical Formula 21:

[Chemical Formula 7]

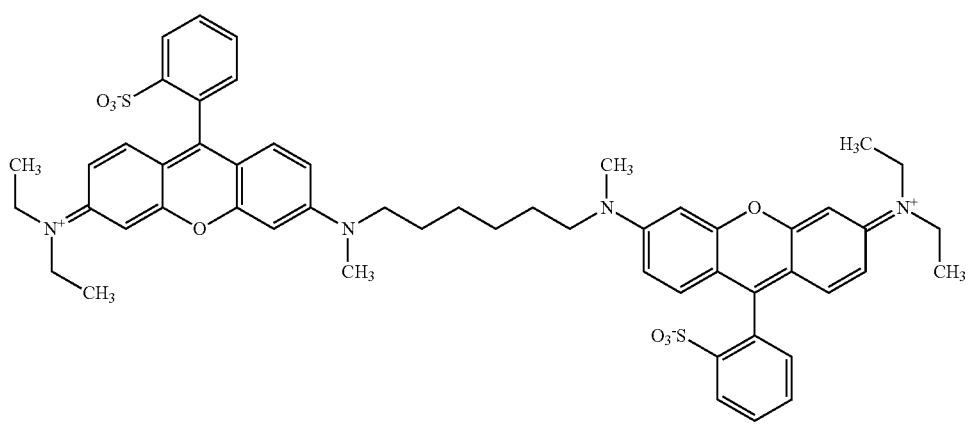

[Chemical Formula 8]
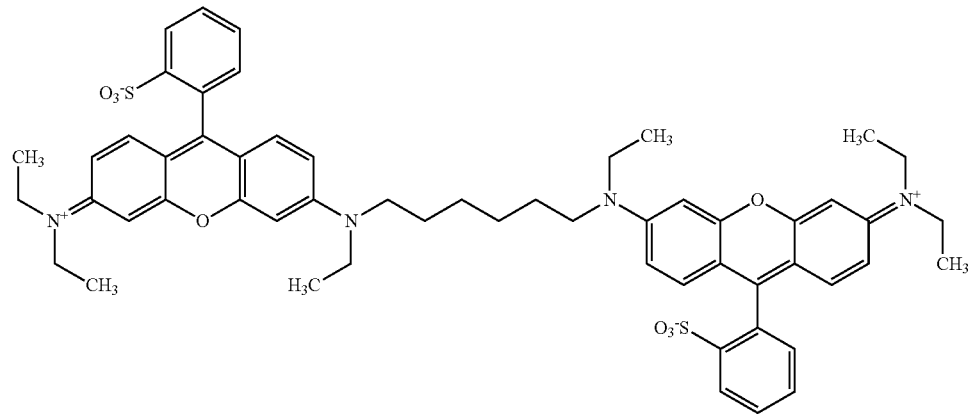
[Chemical Formula 9]
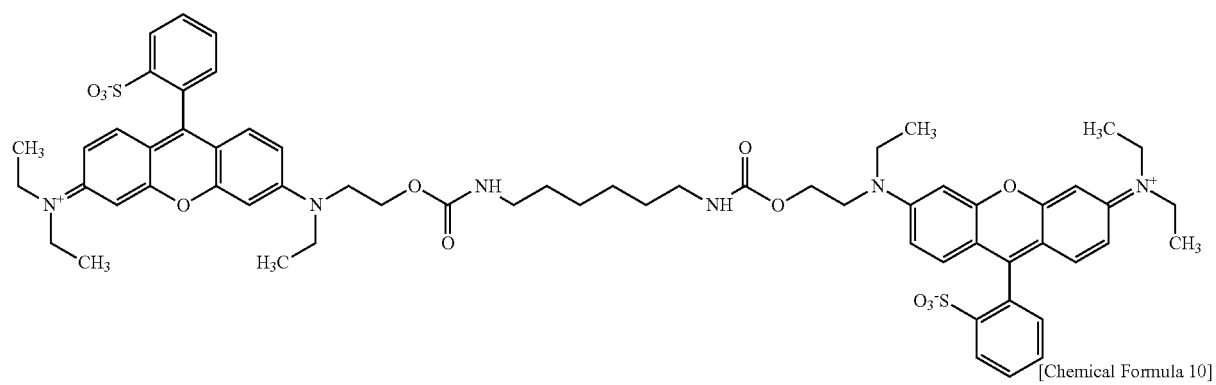
[Chemical Formula 10]
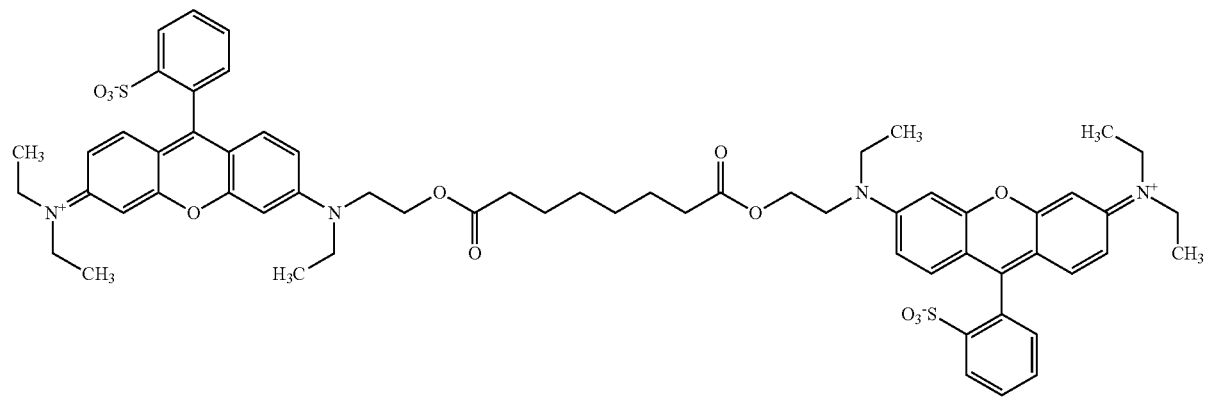
[Chemical Formula 11]
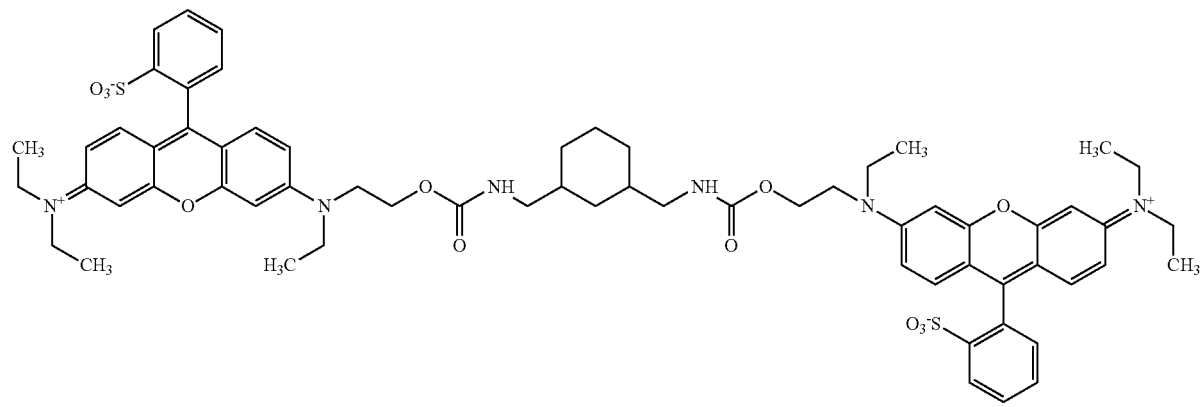

-continued
[Chemical Formula 12]
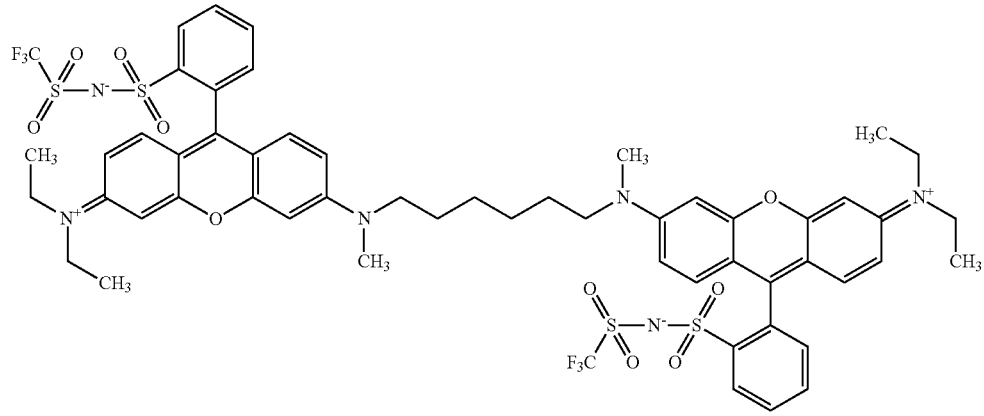
[Chemical Formula 13]
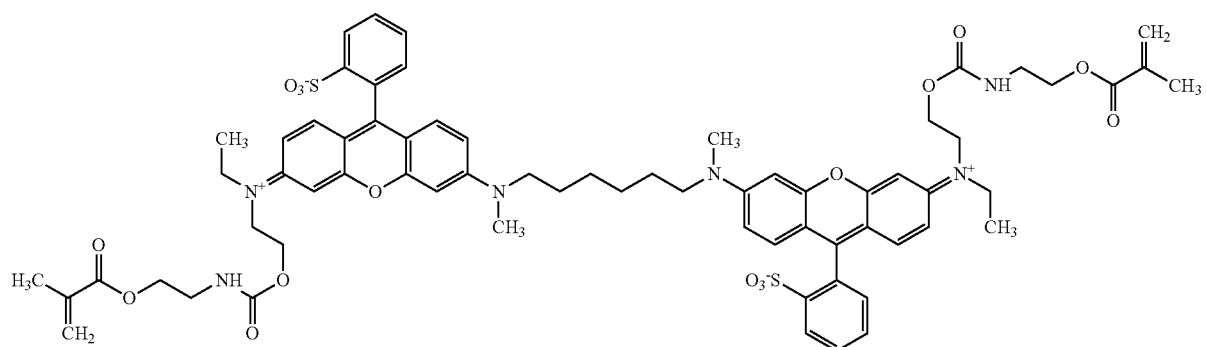
[Chemical Formula 14]
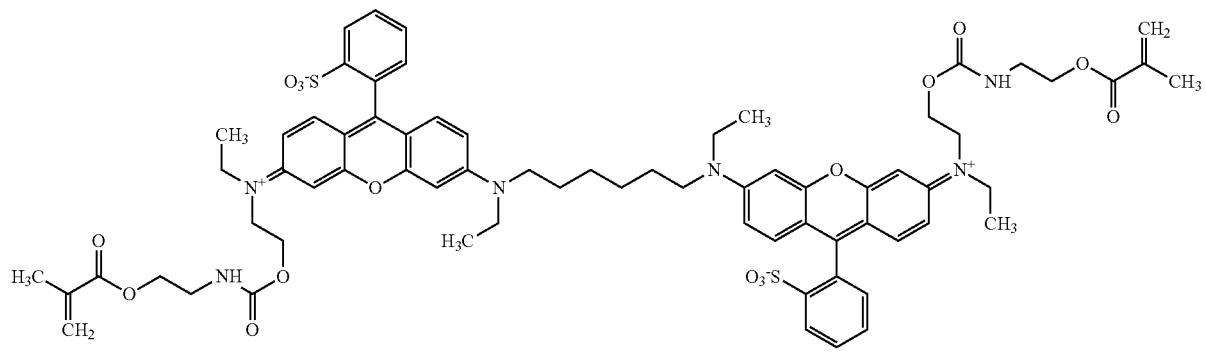
[Chemical Formula 15]
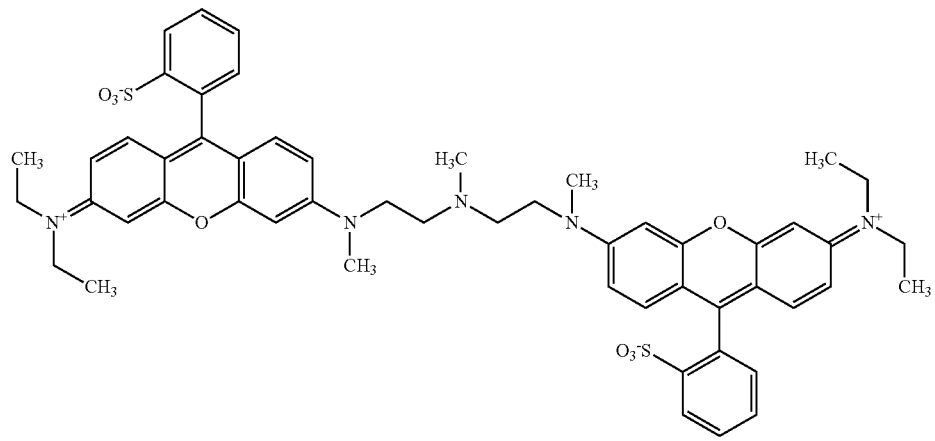

-continued
[Chemical Formula 16]
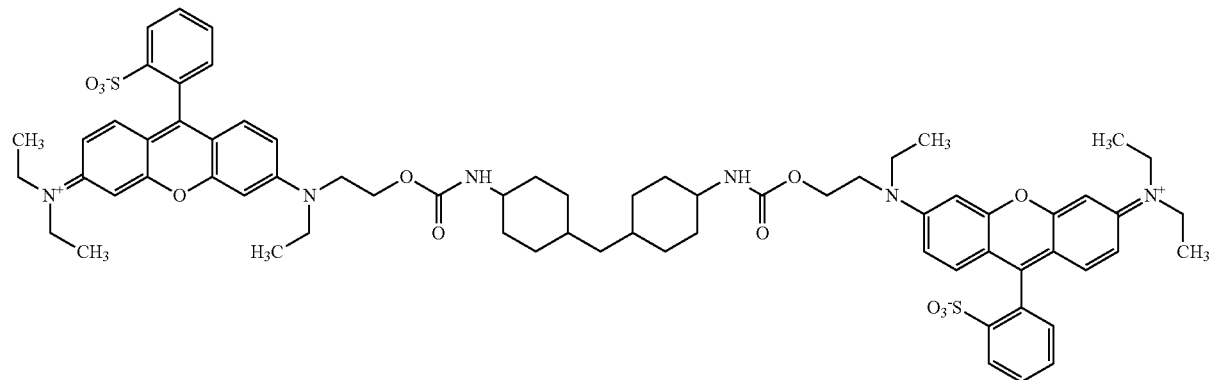
[Chemical Formula 17]
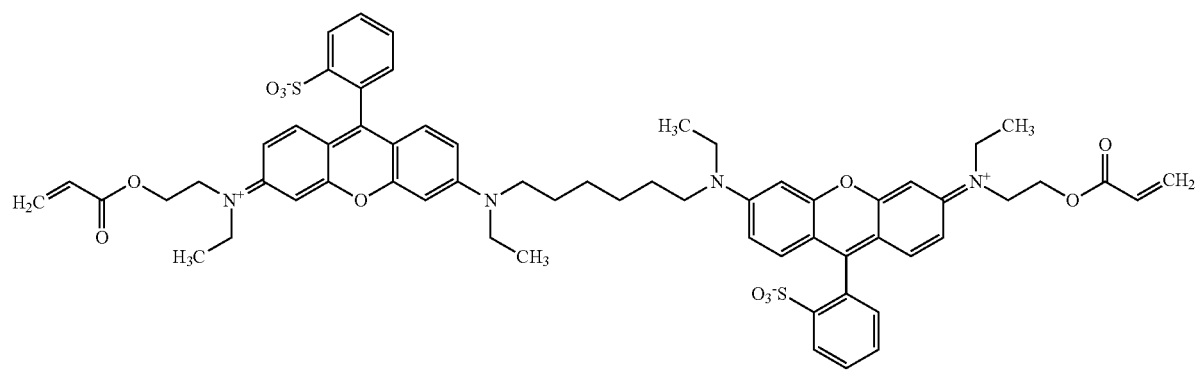
[Chemical Formula 18]
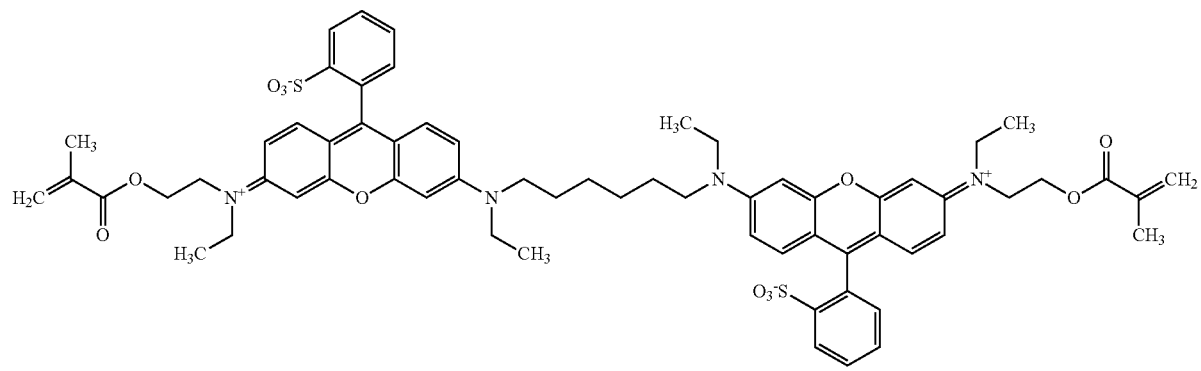
[Chemical Formula 19]
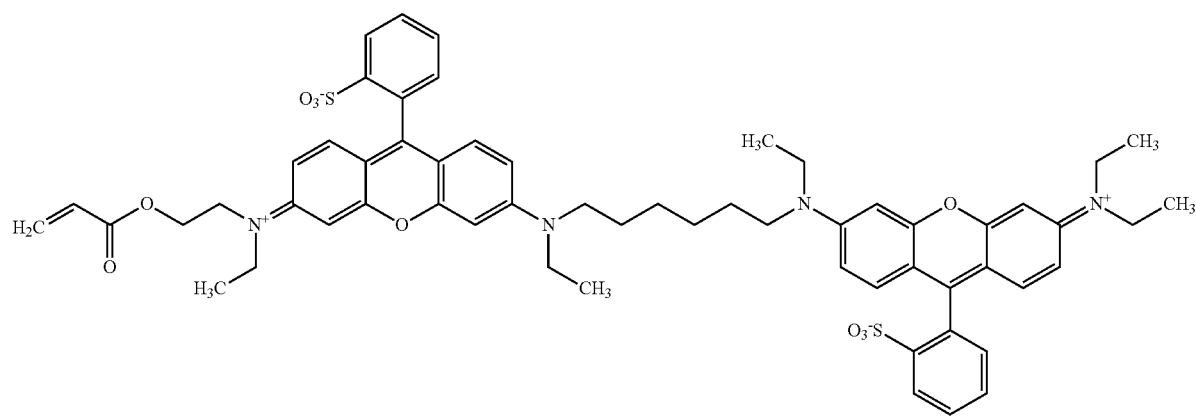

[Chemical Formula 20]

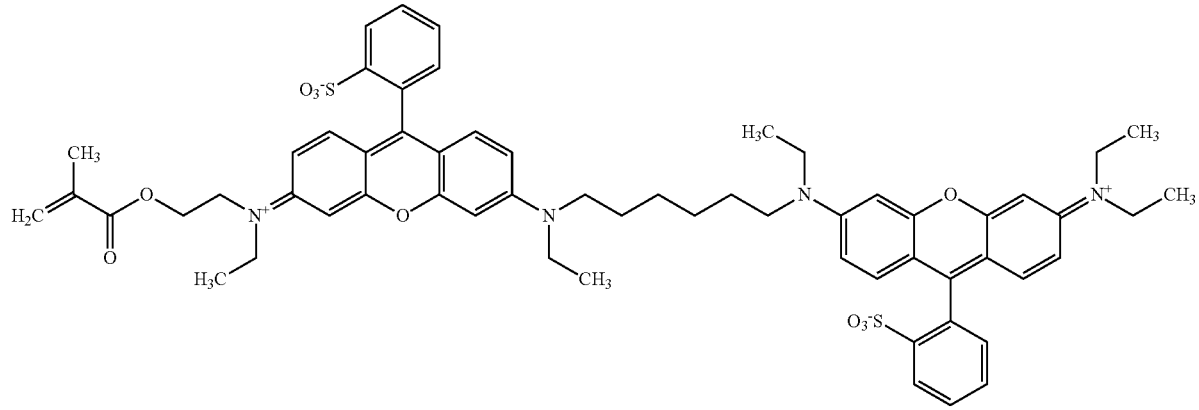

[Chemical Formula 21]

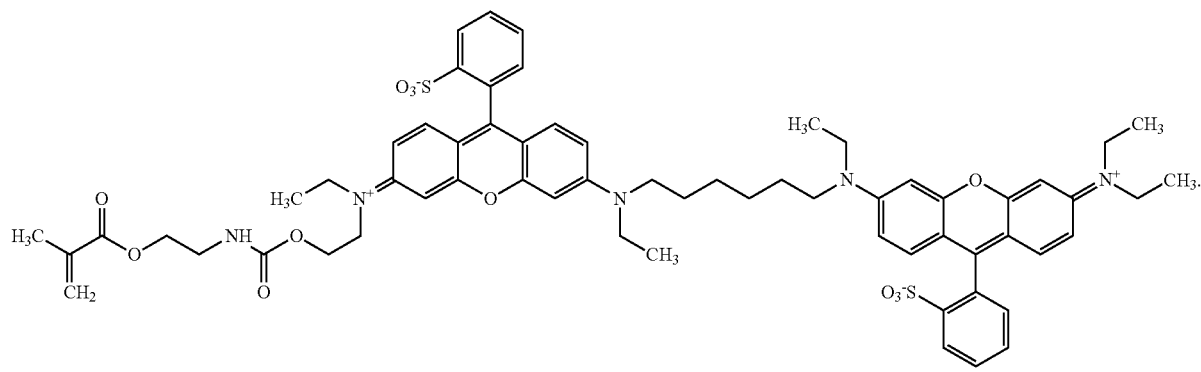

The compound represented by Chemical Formula 1 may have a maximum absorbance in a wavelength range of about 500 nm to about 600 nm.

The embodiments may be realized by providing a photosensitive resin composition including the compound according to an embodiment.

The compound may be included in an amount of about 5 wt % to about 10 wt %, based on a total weight of the photosensitive resin composition.

The compound may be a red dye or a blue dye.

The photosensitive resin composition may further include a binder resin, a photopolymerizable compound, a photopolymerization initiator, and a solvent.

The binder resin may include an acryl binder resin, a cardo binder resin, or a combination thereof.

The photosensitive resin composition may further include a pigment along with the compound as a colorant.

The photosensitive resin composition may include about 1 wt % to about 10 wt % of the binder resin; about 5 wt % to about 60 wt % of the colorant; about 1 wt % to about 10 wt % of the photopolymerizable compound; about 0.01 wt % to about 5 wt % of the photopolymerization initiator; and the solvent, all wt % being based on a total weight of the photosensitive resin composition.

The photosensitive resin composition may further include malonic acid, 3-amino-1,2-propanediol, a silane-based coupling agent including a vinyl group or a (meth)acryloxy group, a leveling agent, a surfactant, a radical polymerization initiator, or a combination thereof.

The embodiments may be realized by providing a color filter manufactured using the photosensitive resin composition according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
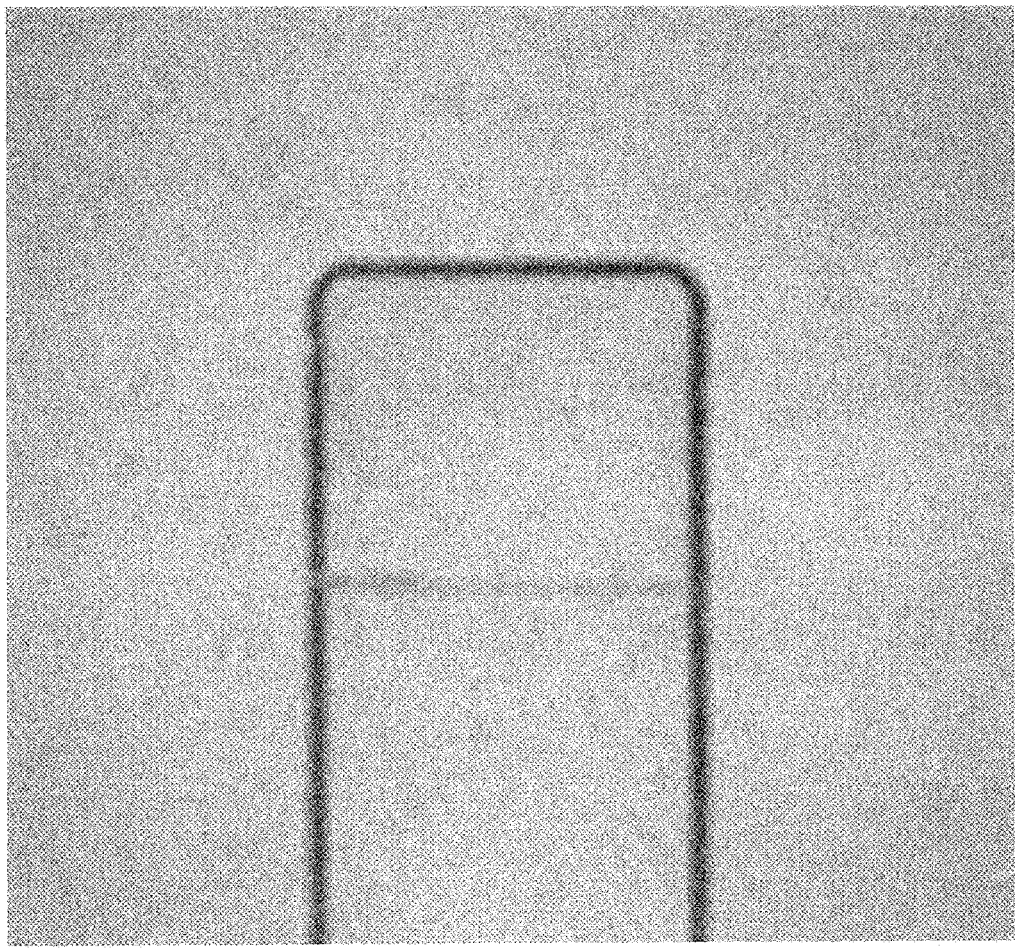
FIG. 1 illustrates a pattern image of the specimen manufactured using the photosensitive resin composition according to Example 2.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present.

As used herein, when specific definition is not otherwise provided, "substituted" refers to replacement of at least one hydrogen atom of a group with at least one substituent selected from a halogen atom (F, Br, Cl, or I), a hydroxy group, a nitro group, a cyano group, an amino group ($NH_2$, $NH(R^{200})$, or $N(R^{201})(R^{202})$, wherein $R^{200}$, $R^{201}$, and $R^{202}$ are the same or different, and are independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, and a substituted or unsubstituted heterocyclic group.

As used herein, when specific definition is not otherwise provided, "alkyl group" refers to a C1 to C20 alkyl group, e.g., a C1 to C15 alkyl group, "cycloalkyl group" refers to a C3 to C20 cycloalkyl group, e.g., a C3 to C18 cycloalkyl group, "alkoxy group" refers to a C1 to C20 alkoxy group, e.g., a C1 to C18 alkoxy group, "aryl group" refers to a C6 to C20 aryl group, e.g., to C18 aryl group, "alkenyl group" refers to a C2 to C20 alkenyl group, e.g., a C2 to C18 alkenyl group, "alkylene group" refers to a C1 to C20 alkylene group, e.g., a C1 to C18 alkylene group, and "arylene group" refers to a C6 to C20 arylene group, e.g., a C6 to C16 arylene group.

As used herein, when specific definition is not otherwise provided, "(meth)acrylate" refers to both "acrylate" and "methacrylate" and "(meth)acrylic acid" refers to both "acrylic acid" and "methacrylic acid".

As used herein, when a definition is not otherwise provided, the term "combination" refers to mixing or copolymerization. In addition, "copolymerization" refers to block copolymerization to random copolymerization and "copolymer" refers to a block copolymer to a random copolymer.

As used herein, when a definition is not otherwise provided, in chemical formula, hydrogen is bonded at the position when a chemical bond is not drawn where supposed to be given.

As used herein, a cardo resin refers to a resin including at least one functional group selected from Chemical Formula 22-1 to Chemical Formula 22-11 in its backbone.

As used herein, when a definition is not otherwise provided, "ethylenic unsaturated double bond" refers to "a carbon-carbon double bond" and an ethylenic unsaturated monomer refers to a monomer including the ethylenic unsaturated double bond.

As used herein, when specific definition is not otherwise provided, "*" indicates a point where the same or different atom or chemical formula is linked. As used herein, the term "or" is not an exclusive term, e.g., "A or B" would include A, B, and A and B.

An embodiment provides a compound represented by Chemical Formula 1.

[Chemical Formula 1]

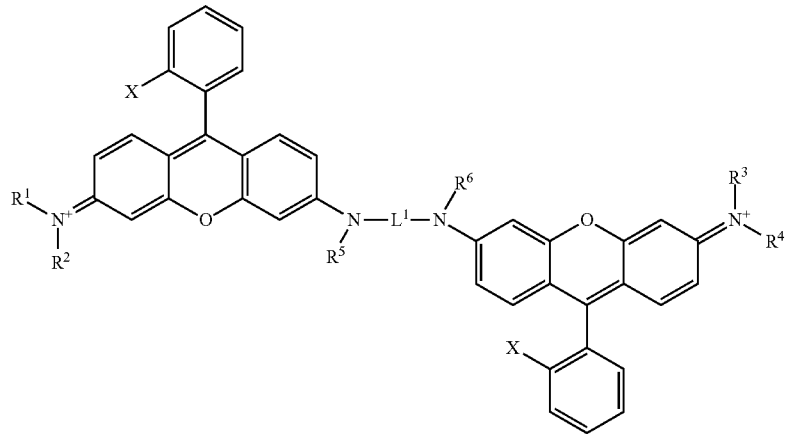

In Chemical Formula 1, $R^1$ to $R^6$ may each independently be or include, e.g., a hydrogen atom, a substituted or unsubstituted C1 to C20 alkyl group, or a substituted or unsubstituted C6 to C20 aryl group, $L^1$ may be or may include, e.g., a substituted or unsubstituted C1 to C20 alkylene group, a substituted or unsubstituted C3 to C20 cycloalkylene group, a substituted or unsubstituted C6 to C20 arylene group, *—OC(=O)NH—*, *—O(C=O)—*, *—$NR^x$—*, or a combination thereof, the $R^x$ is a substituted or unsubstituted C1 to C10 alkyl group, and X may be a group represented by, e.g., Chemical Formula X-1 or Chemical Formula X-2.

[Chemical Formula X-1]

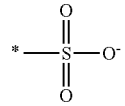

[Chemical Formula X-2]

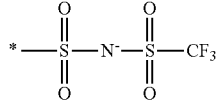

As described above, a color filter manufactured by using a pigment-type photosensitive resin composition could have a limit in terms of luminance and a contrast ratio due to a pigment particle size. In addition, a color image sensor device for an image sensor may require a smaller dispersion particle diameter to form a fine pattern. In order to correspond to the requirements, an attempt to realize a color filter having improved luminance and a contrast ratio has been made by introducing a dye (forming no particle), instead of the pigment, to prepare a photosensitive resin composition appropriate for the dye.

A photosensitive resin composition including a xanthene-based compound in which a charge is separated may have very low solubility in an organic solvent (such as PGMEA) and may exhibit deteriorated heat resistance and chemical resistance. The xanthene-based compound as a colorant may have a limit of being used in the photosensitive resin composition. The compound according to an embodiment, e.g., the compound represented by Chemical Formula 1 may exhibit improved solubility in an organic solvent and in addition, may have a dimeric structure linked by a functional linking group and thus excellent fluorescence quenching properties and spectroscopic coherence, and resultantly, a photosensitive resin composition including the same may help improve luminance and a contrast ratio of a color filter.

In an implementation, $L^1$ may be a group represented by Chemical Formula 2.

[Chemical Formula 2]

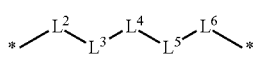

In Chemical Formula 2, $L^2$ to $L^6$ may each independently be or include, e.g., a single bond, a substituted or unsubstituted C1 to C10 alkylene group, a substituted or unsubstituted C3 to C20 cycloalkylene group, *—OC(=O)NH—*, *—O(C=O)—* or *—NR$^x$—*, in which R$^x$ is a substituted or unsubstituted C1 to C10 alkyl group. In an implementation, all of $L^2$ to $L^6$ are not a single bond.

In an implementation, $L^1$ may be a substituted or unsubstituted C1 to C20 alkylene group.

In an implementation, $L^1$ (e.g., the group represented by Chemical Formula 2) may be e.g., a group represented by Chemical Formula 3.

[Chemical Formula 3]

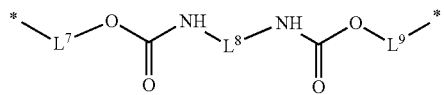

In Chemical Formula 3, $L^7$ to $L^9$ may each independently be or include, e.g., a substituted or unsubstituted C1 to C10 alkylene group, a substituted or unsubstituted C3 to C10 cycloalkylene group, or a combination thereof.

In an implementation, $L^7$ to $L^9$ may each independently be or include, e.g., a substituted or unsubstituted C1 to C10 alkylene group or a group represented by Chemical Formula 3-1 or Chemical Formula 3-2.

[Chemical Formula 3-1]

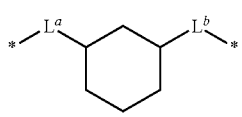

[Chemical Formula 3-2]

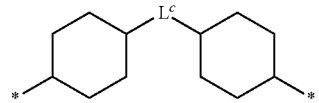

In Chemical Formula 3-1 and Chemical Formula 3-2, $L^a$ to $L^c$ may each independently be or include, e.g., a substituted or unsubstituted C1 to C5 alkylene group.

In an implementation, $L^1$ (e.g., the group represented by Chemical Formula 2) may be e.g., a group represented Chemical Formula 4.

[Chemical Formula 4]

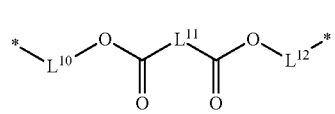

In Chemical Formula 4, $L^{10}$ to $L^{12}$ may each independently be or include. e.g., a substituted or unsubstituted C1 to C10 alkylene group.

In an implementation, $L^1$ (e.g., the group represented by Chemical Formula 2) may be e.g., a group represented Chemical Formula 5.

[Chemical Formula 5]

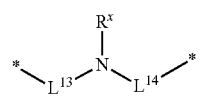

In Chemical Formula 5, $L^{13}$ and $L^{14}$ may each independently be or include, e.g., a substituted or unsubstituted C1 to C10 alkylene group, and R$^x$ may be or may include, e.g., a substituted or unsubstituted C1 to C10 alkyl group.

In an implementation, at least one of $R^1$ to $R^4$ may be a group represented by Chemical Formula 6-1 or Chemical Formula 6-2. For example, at least one of $R^1$ to $R^4$ may be a substituted C1 to C10 alkyl group.

[Chemical Formula 6-1]

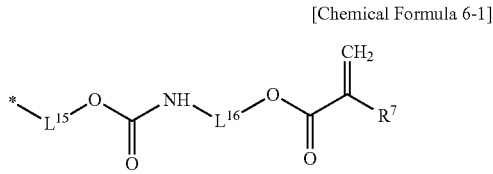

[Chemical Formula 6-2]

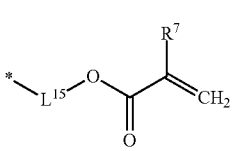

In Chemical Formula 6-1 and Chemical Formula 6-2, $R^7$ may be or may include, e.g., a hydrogen atom or a substituted or unsubstituted C1 to C10 alkyl group, and $L^{15}$ and $L^{16}$ may each independently be or include, e.g., a substituted or unsubstituted C1 to C10 alkylene group.

In an implementation, one of $R^1$ to $R^4$ may be a group represented by Chemical Formula 6-1 or Chemical Formula 6-2.

In an implementation, two of $R^1$ to $R^4$ may be a group represented by Chemical Formula 6-1 or Chemical Formula 6-2.

In an implementation, one of $R^1$ and $R^2$ and one of $R^3$ and $R^4$ may be a group represented by Chemical Formula 6-1 or Chemical Formula 6-2.

When at least one of $R^1$ to $R^4$ is a group represented by Chemical Formula 6-1 or Chemical Formula 6-2, solubility in an organic solvent may be further improved.

When at least one of $R^1$ to $R^4$ is a group represented by Chemical Formula 6-1 or Chemical Formula 6-2, a copolymerization reaction between the compound represented by Chemical Formula 1 and a monomer may occur to form a polymer. For example, the monomer may be an ethylenic unsaturated monomer and the polymer may be an acrylic polymer.

For example, the ethylenic unsaturated monomer may be an aromatic vinyl compound, an unsaturated carboxylate ester compound, a unsaturated amino alkyl carboxylate ester compound, a vinyl carboxylate ester compound, a unsaturated glycidyl carboxylate ester compound, a vinyl cyanide compound, a unsaturated amide compound, or a combination thereof.

For example, the ethylenic unsaturated monomer may be an aromatic vinyl compound such as styrene, α-methylstyrene, vinyltoluene, vinylbenzylmethylether, and the like; an unsaturated carboxylate ester compound such as (meth)acrylate, methyl(meth)acrylate, ethyl(meth)acrylate, butyl (meth)acrylate, 2-ethylhexyl acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; an unsaturated carboxylic acid amino alkyl ester compound such as 2-aminoethyl(meth)acrylate, 2-dimethylaminoethyl(meth)acrylate, and the like; a carboxylic acid vinyl ester compound such as vinyl acetate, vinyl benzoate, and the like; an unsaturated carboxylic acid glycidyl ester compound such as glycidyl(meth)acrylate, and the like; a vinyl cyanide compound such as (meth)acrylonitrile, and the like; an unsaturated amide compound such as (meth)acrylamide, and the like, or a combination thereof.

An acrylic polymer as a polymerization reaction product of a copolymerization of the compound represented by Chemical Formula 1 wherein at least one of $R^1$ to $R^4$ is a group represented by Chemical Formula 6-1 or Chemical Formula 6-2 and the ethylenic unsaturated monomer may exhibit improved heat resistance and processability, and may be used as a colorant, e.g., a dye in a photosensitive resin composition for a color filter.

In an implementation, the compound represented by Chemical Formula 1 may be, e.g., a compound represented by one of Chemical Formula 7 to Chemical Formula 21.

[Chemical Formula 7]

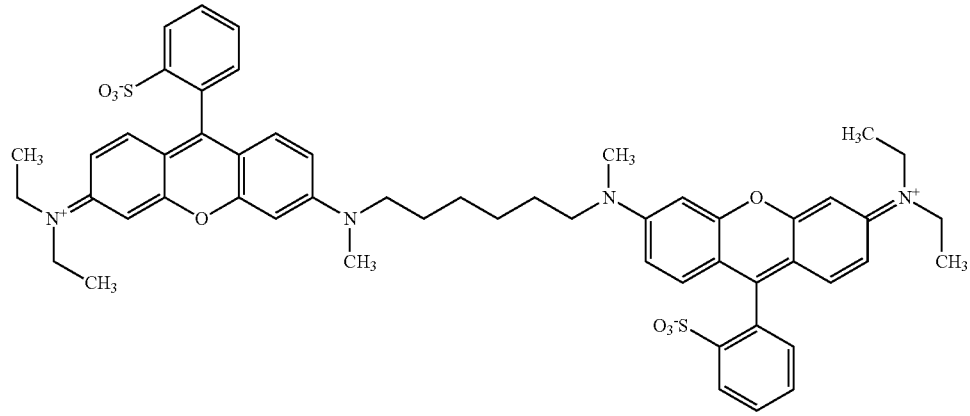

[Chemical Formula 8]

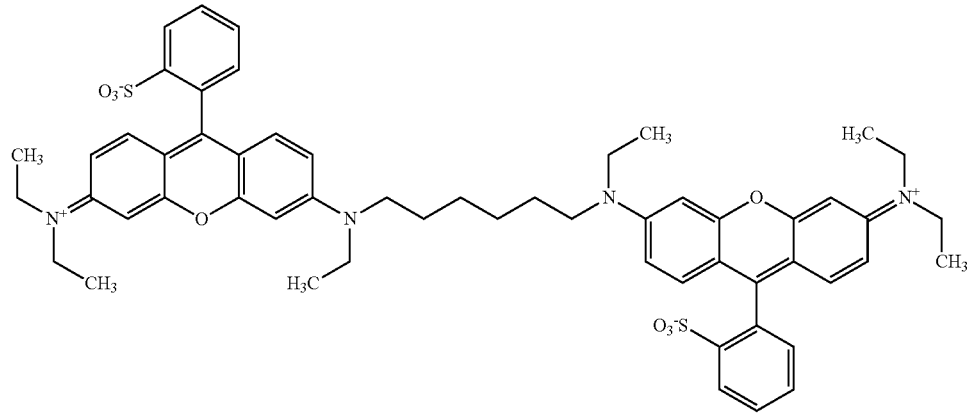

[Chemical Formula 9]
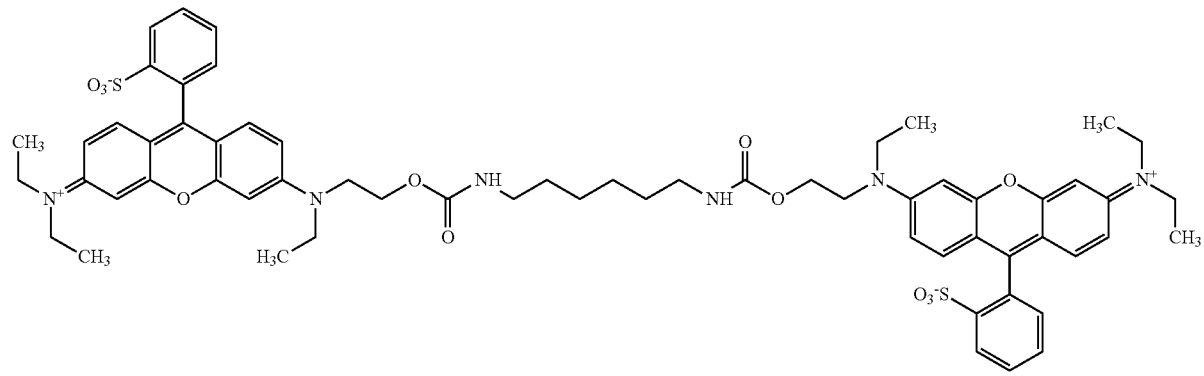
[Chemical Formula 10]
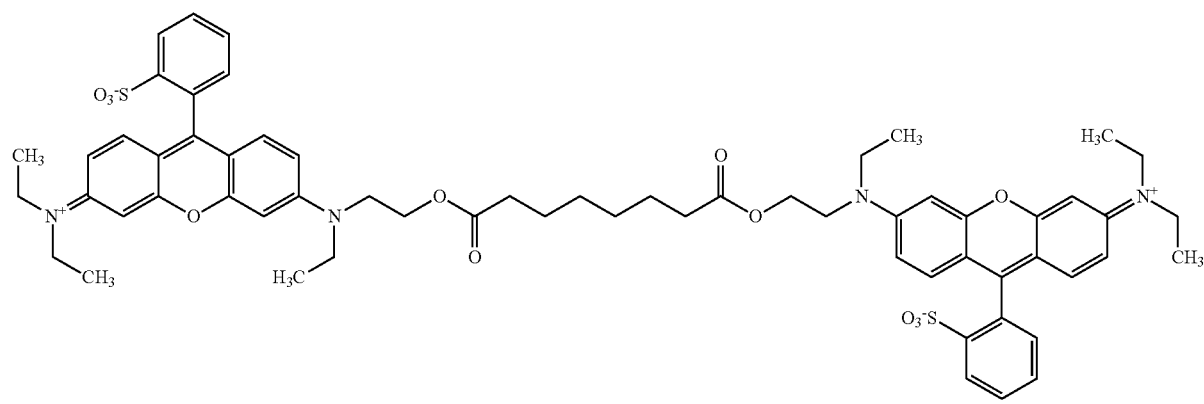
[Chemical Formula 11]
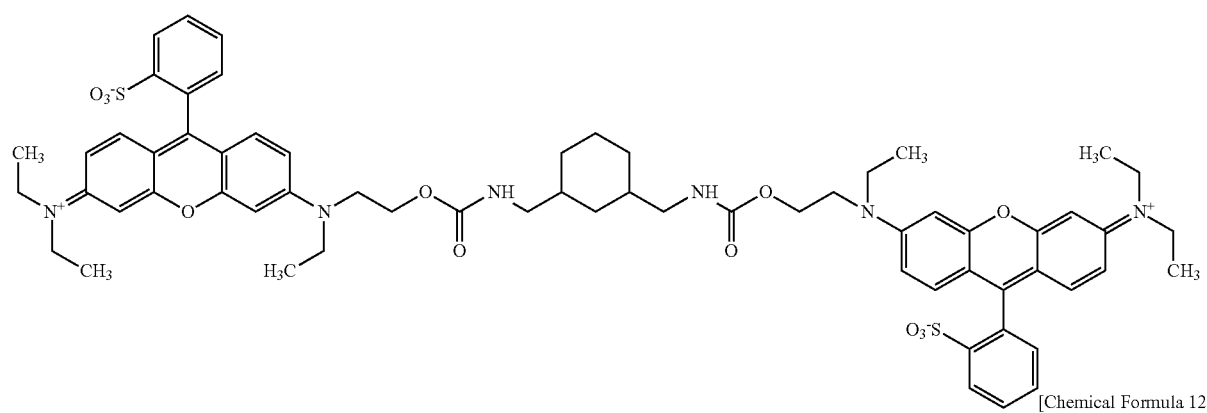
[Chemical Formula 12]
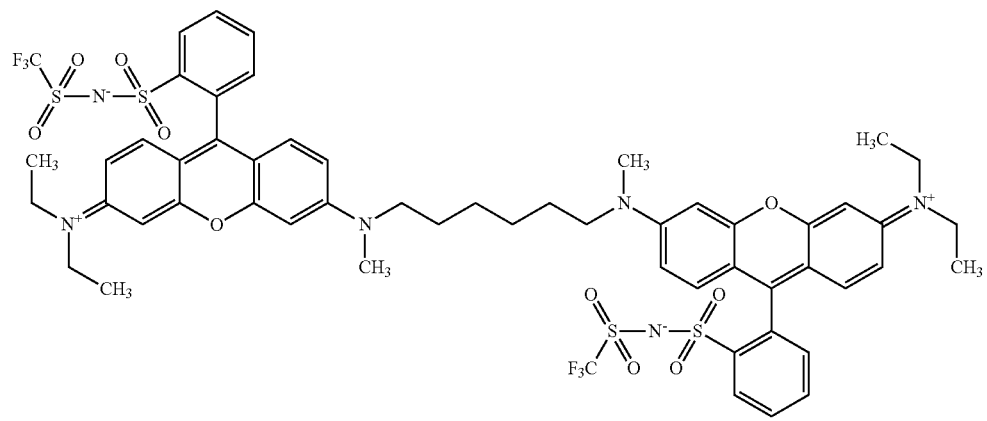

-continued
[Chemical Formula 13]
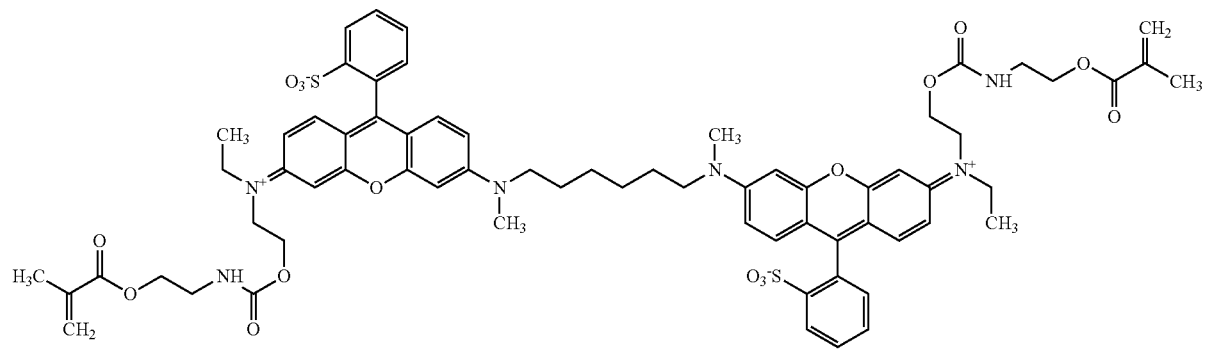
[Chemical Formula 14]
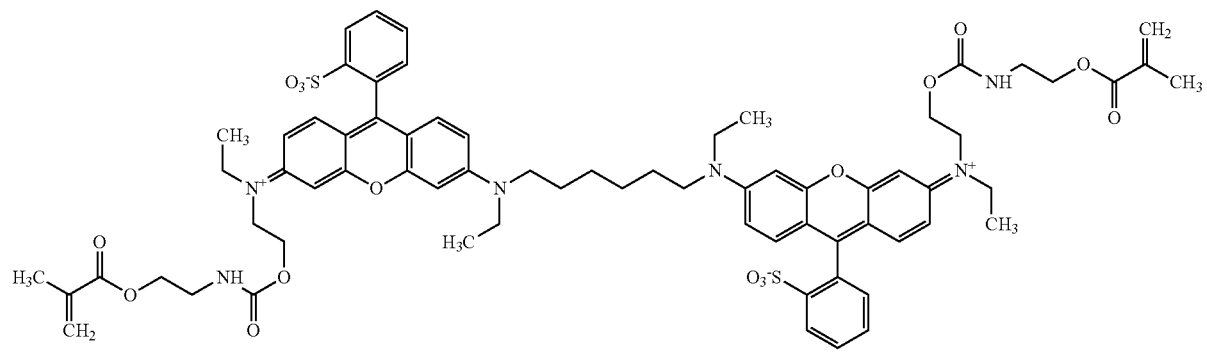
[Chemical Formula 15]
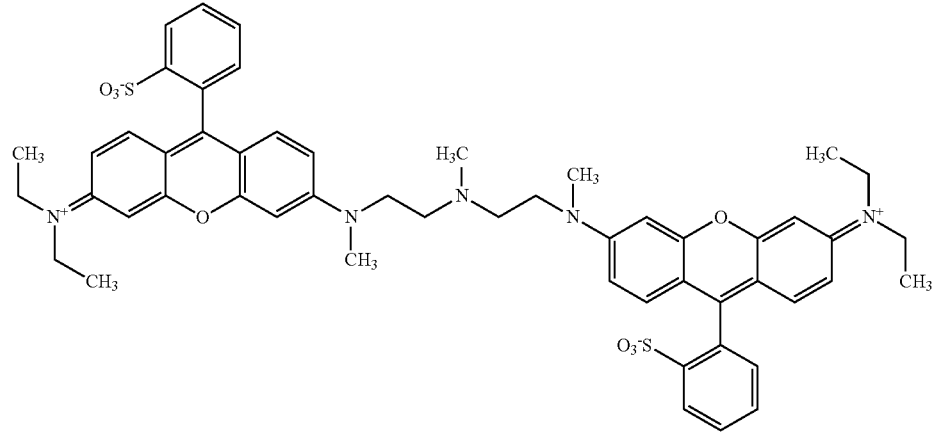
[Chemical Formula 16]
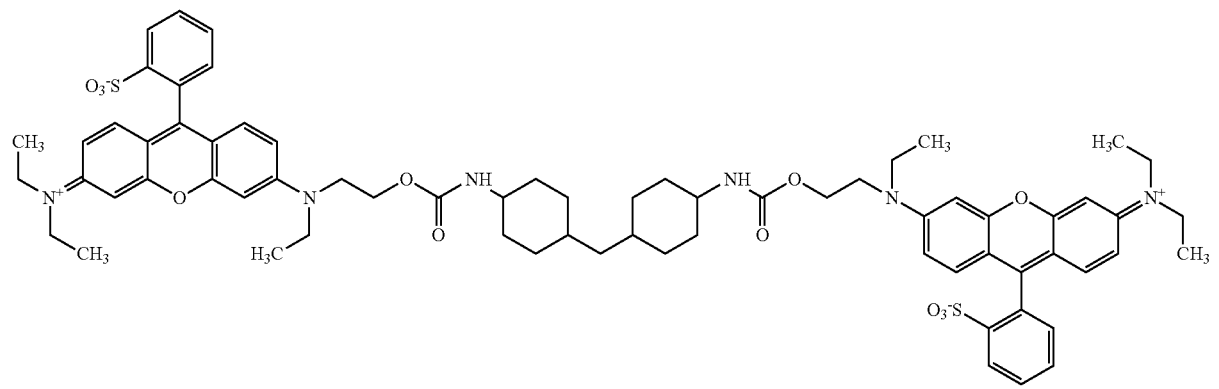

[Chemical Formula 17]
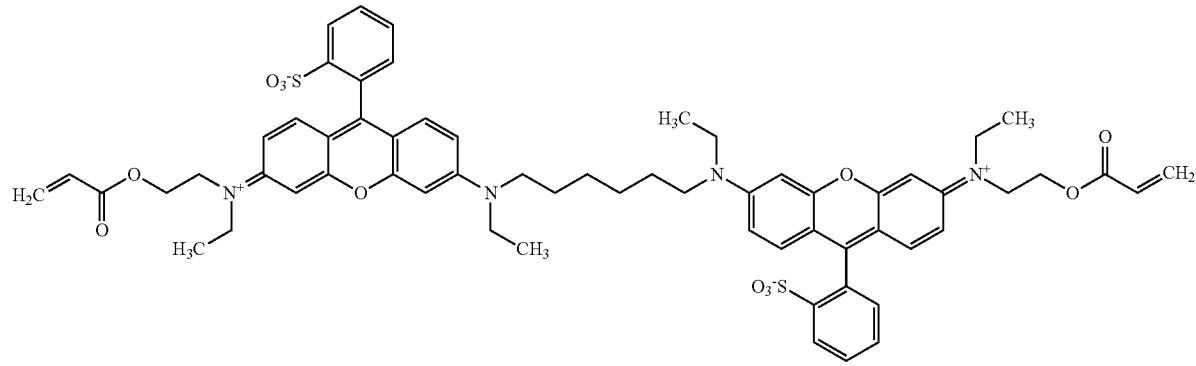
[Chemical Formula 18]
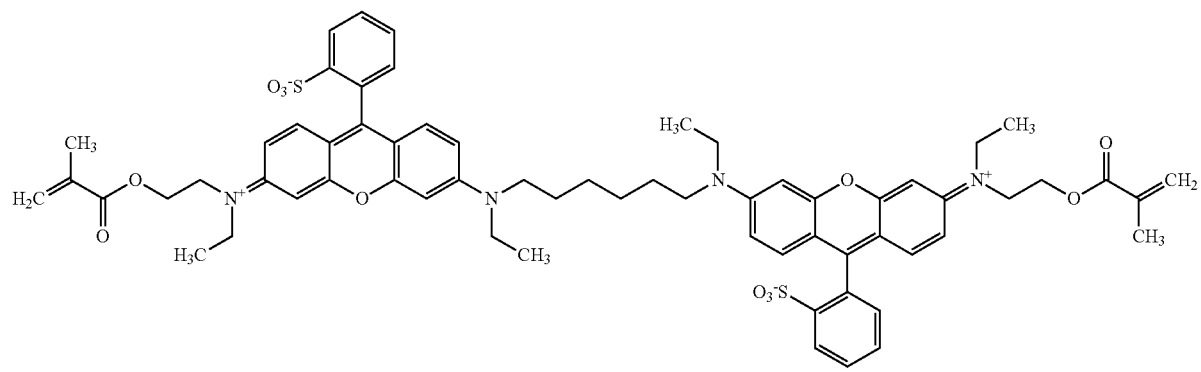
[Chemical Formula 19]
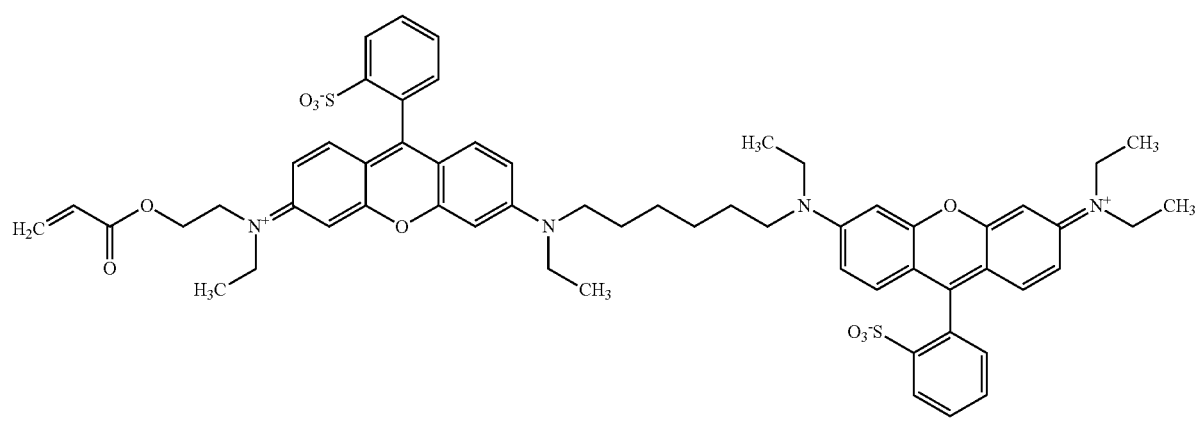
[Chemical Formula 20]
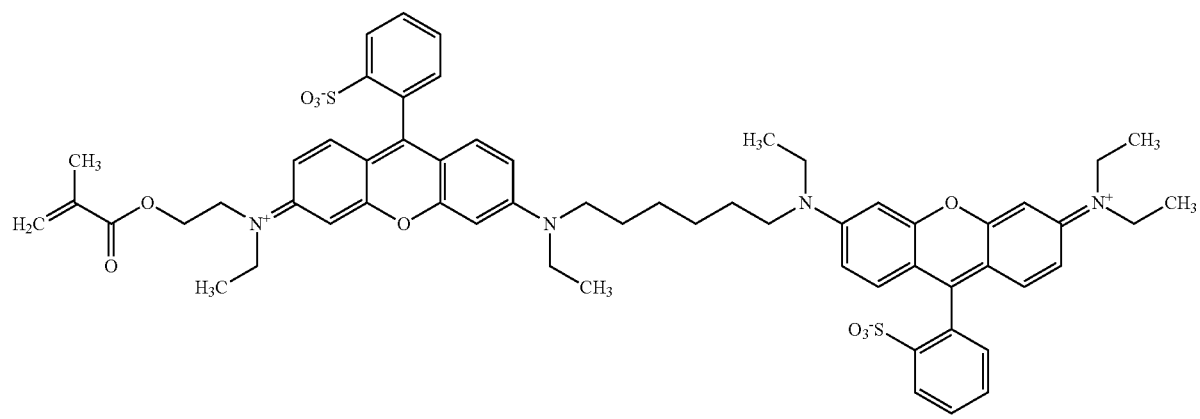

[Chemical Formula 21]

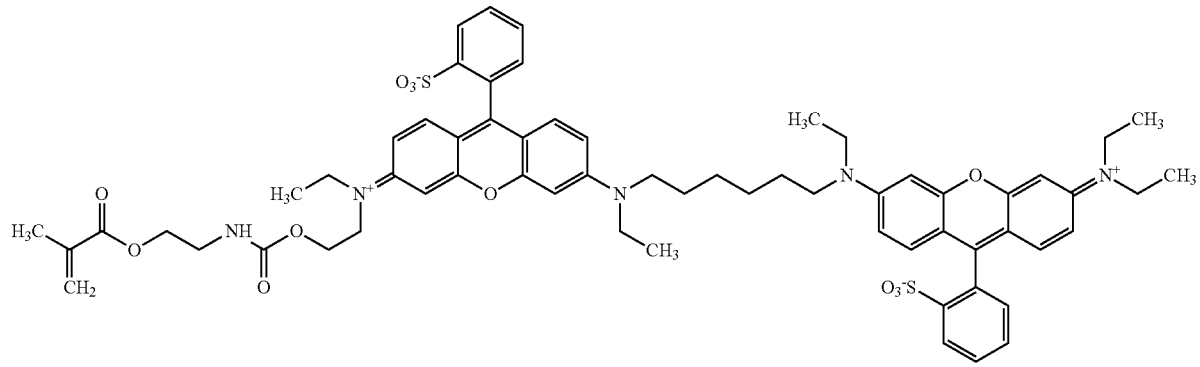

The compound represented by Chemical Formula 1 may have a maximum absorbance in a wavelength range of about 500 nm to about 600 nm.

Another embodiment provides a photosensitive resin composition including the compound (represented by Chemical Formula 1) as a colorant.

In an implementation, the compound may be included in an amount of about 5 wt % to about 10 wt %, e.g. about 6 wt % to about 9 wt % or about 6 wt % to about 8 wt %, based on a total weight of the photosensitive resin composition, and thereby luminance, heat resistance, and pattern characteristics may be further improved.

The compound may be a red dye or a blue dye.

The photosensitive resin composition may further include a binder resin, a photopolymerizable compound, a photopolymerization initiator, and a solvent.

Hereinafter, each component is specifically described.

Colorant

The colorant may further include an organic solvent-soluble dye in addition to the compound represented by Chemical Formula 1.

Examples of the organic solvent-soluble dye may include a triarylmethane-based compound, an anthraquinone-based compound, a benzylidene-based compound, a cyanine-based compound, a phthalocyanine-based compound, an azaporphyrin-based compound, an indigo-based compound, and the like.

The colorant may further include a pigment in addition to the compound represented by Chemical Formula 1.

The pigment may include a blue pigment, a violet pigment, a red pigment, a green pigment, a yellow pigment, or the like.

Examples of the blue pigment may include C.I. blue pigment 15:6, C.I. blue pigment 15, C.I. blue pigment 15:1, C.I. blue pigment 15:2, C.I. blue pigment 15:3, C.I. blue pigment 15:4, C.I. blue pigment 15:5, C.I. blue pigment 16, C.I. blue pigment 22, C.I. blue pigment 60, C.I. blue pigment 64, C.I. blue pigment 80, or a combination thereof.

Examples of the violet pigment may include C.I. violet pigment 1, C.I. violet pigment 19, C.I. violet pigment 23, C.I. violet pigment 27, C.I. violet pigment 28, C.I. violet pigment 29, C.I. violet pigment 30, C.I. violet pigment 32, C.I. violet pigment 37, C.I. violet pigment 40, C.I. violet pigment 42, C.I. violet pigment 50, or a combination thereof.

Examples of the red pigment may include a perylene-based pigment, an anthraquinone-based pigment, a dianthraquinone-based pigment, an azo-based pigment, a diazo-based pigment, a quinacridone-based pigment, an anthracene-based pigment, and the like. Specific examples of the red pigment may include a perylene pigment, a quinacridone pigment, naphthol AS, a sicomin pigment, an anthraquinone (sudan I, II, III, R), dianthraquinonylate, vis azo, benzopyrane, and the like.

Examples of the green pigment may include a halogenated phthalocyanine-based pigment such as C.I. pigment green 58, C.I. pigment green 59, and the like.

Examples of the yellow pigment may include a C.I. pigment yellow 139, a C.I. pigment yellow 138, a C.I. pigment yellow 150, and the like.

The pigments may be used alone or as a mixture of two or more.

The pigment may be included in a form of pigment dispersion liquid in the photosensitive resin composition.

The pigment dispersion liquid may include a solid pigment, a solvent, and a dispersing agent in order to disperse the pigment in the solvent uniformly.

In an implementation, the pigment may be included in a solid content of about 1 wt % to about 20 wt %, e.g., about 8 wt % to about 20 wt %, about 8 wt % to about 15 wt %, about 10 wt % to about 20 wt %, or about 10 wt % to about 15 wt %, based on a total weight of pigment dispersion liquid.

The dispersing agent may be a non-ionic dispersing agent, an anionic dispersing agent, a cationic dispersing agent, and the like. Specific examples of the dispersing agent may include polyalkylene glycol and esters thereof, polyoxyalkylene, polyhydric alcohol ester alkylene oxide addition product, alcoholalkylene oxide addition product, sulfonate ester, sulfonate salt, a carboxylate ester, a carboxylate salt, an alkylamide alkylene oxide addition product, alkyl amine, and the like, and may be used alone or as a mixture of two or more.

Commercially available examples of the dispersing agent may include DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; or PB711, or PB821 made by Ajinomoto Inc.

The dispersing agent may be included in an amount of about 1 wt % to about 20 wt %, based on a total weight of the pigment dispersion liquid. When the dispersing agent is included within the range, dispersion of a photosensitive resin composition is improved due to an appropriate viscosity, and thus optical, physical, and chemical quality may be maintained when the photosensitive resin composition is applied to products.

The solvent for forming the pigment dispersion liquid may include, e.g., ethylene glycol acetate, ethylcellosolve, propylene glycol monomethyl ether acetate, ethyllactate, polyethylene glycol, cyclohexanone, propylene glycol methylether, or the like.

In an implementation, the colorant may be included in an amount of about 5 wt % to about 60 wt %, e.g., about 6 wt % to about 55 wt %, based on the total weight of the photosensitive resin composition. When the colorant is included within the ranges, color reproducibility may be improved and curability of a pattern and close contacting properties may be improved.

Binder Resin

The binder resin may include, e.g., an acryl binder resin, a cardo binder resin, or a combination thereof. For example, the binder resin may include an acryl binder resin.

In an implementation, the acryl binder resin may include, e.g., a polybenzylmethacrylate copolymer, an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, or the like. These may be used singularly or as a mixture of two or more.

The acryl binder resin may have a weight average molecular weight of about 3,000 g/mol to about 150,000 g/mol, e.g., about 5,000 g/mol to about 50,000 g/mol, or about 20,000 g/mol to about 30,000 g/mol. When the acryl-based binder resin has a weight average molecular weight within the range, the photosensitive resin composition may exhibit good physical and chemical properties, appropriate viscosity, and close contacting properties with a substrate during manufacture of a color filter.

The acryl-based binder resin may have an acid value of about 15 mgKOH/g to about 60 mgKOH/g, e.g., about 20 mgKOH/g to about 50 mgKOH/g. When the acryl-based binder resin has an acid value within the range, a pixel pattern may have excellent resolution.

The cardo binder resin may include a repeating unit represented by Chemical Formula 22.

[Chemical Formula 22]

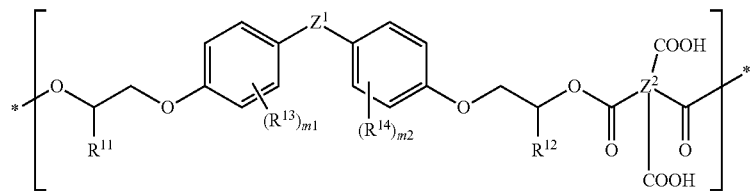

The acryl binder resin may be a copolymer of a first ethylenic unsaturated monomer and a second ethylenic unsaturated monomer that is copolymerizable therewith, and is resin including at least one acryl repeating unit.

In an implementation, the first ethylenic unsaturated monomer may be an ethylenic unsaturated monomer including at least one carboxyl group. Examples of the monomer may include (meth)acrylic acid, maleic acid, itaconic acid, fumaric acid, or a combination thereof.

The first ethylenic unsaturated monomer may be included in an amount of about 5 wt % to about 50 wt %, e.g., about 10 wt % to about 40 wt %, based on the total weight of the acryl binder resin.

The second ethylenic unsaturated monomer may be an aromatic vinyl compound such as styrene, α-methylstyrene, vinyl toluene, vinylbenzylmethylether or the like; an unsaturated carboxylate ester compound such as methyl(meth)acrylate, ethyl(meth)acrylate, butyl(meth)acrylate, 2-hydroxyethyl(meth)acrylate, 2-hydroxy butyl(meth)acrylate, benzyl(meth)acrylate, cyclohexyl(meth)acrylate, phenyl(meth)acrylate, or the like; an unsaturated amino alkyl carboxylate ester compound such as 2-aminoethyl(meth)acrylate, 2-dimethylaminoethyl(meth)acrylate, or the like; a carboxylic acid vinyl ester compound such as vinyl acetate, vinyl benzoate, or the like; an unsaturated glycidyl carboxylate ester compound such as glycidyl(meth)acrylate, or the like; a vinyl cyanide compound such as (meth)acrylonitrile or the like; an unsaturated amide compound such as (meth)acrylamide, or the like; and may be used alone or as a mixture of two or more.

In Chemical Formula 22, $R^{11}$ and $R^{12}$ may each independently be or include, e.g., a hydrogen atom or a substituted or unsubstituted (meth)acryloyloxyalkyl group, $R^{13}$ and $R^{14}$ may each independently be or include, e.g., a hydrogen atom, a halogen atom, or a substituted or unsubstituted C1 to C20 alkyl group, and $Z^1$ may be, e.g., a single bond, O, CO, $SO_2$, $CR^{15}R^{16}$, $SiR^{17}R^{18}$ (in which $R^{15}$ to $R^{18}$ may each independently be or include, e.g., a hydrogen atom or a substituted or unsubstituted C1 to C20 alkyl group), or a linking group represented by one of Chemical Formula 22-1 to Chemical Formula 22-11,

[Chemical Formula 22-1]

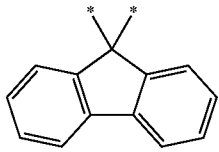

[Chemical Formula 22-2]

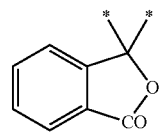

-continued

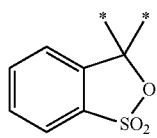
[Chemical Formula 22-3]

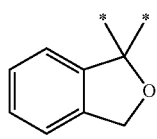
[Chemical Formula 22-4]

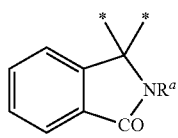
[Chemical Formula 22-5]

wherein, in Chemical Formula 22-5, $R^a$ may be, e.g., a hydrogen atom, an ethyl group, $C_2H_4Cl$, $C_2H_4OH$, $CH_2CH=CH_2$, or a phenyl group.

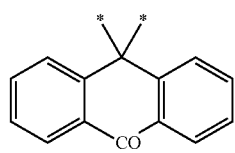
[Chemical Formula 22-6]

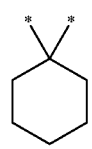
[Chemical Formula 22-7]

[Chemical Formula 22-8]

[Chemical Formula 22-9]

[Chemical Formula 22-10]

[Chemical Formula 22-11]

$Z^2$ may be, e.g., an acid dianhydride residual group, and m1 and m2 may each independently be, e.g., an integer ranging from 0 to 4.

The cardo binder resin may include a functional group represented by Chemical Formula 23 at one or more terminal ends thereof.

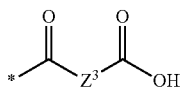
[Chemical Formula 23]

In Chemical Formula 23, $Z^3$ may be a group represented by one of Chemical Formula 23-1 to Chemical Formula 23-7.

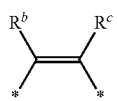
[Chemical Formula 23-1]

In Chemical Formula 23-1, $R^b$ and $R^c$ may each independently be or include, e.g., a hydrogen atom, a substituted or unsubstituted C1 to C20 alkyl group, an ester group, or an ether group.

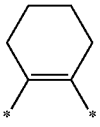
[Chemical Formula 23-2]

[Chemical Formula 23-3]

[Chemical Formula 23-4]

[Chemical Formula 23-5]

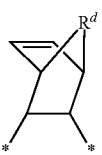

In Chemical Formula 23-5, $R^d$ may be or may include, e.g., O, S, NH, a substituted or unsubstituted C1 to C20 alkylene group, a C1 to C20 alkylamine group, or a C2 to C20 alkenylamine group.

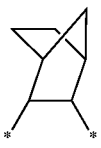
[Chemical Formula 23-6]

-continued

[Chemical Formula 23-7]

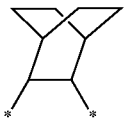

The cardo binder resin may be, e.g., prepared by mixing at least two of, a fluorene-containing compound such as 9,9-bis(4-oxiranylmethoxyphenyl)fluorene; an anhydride compound such as benzenetetracarboxylic acid dianhydride, naphthalenetetracarboxylic acid dianhydride, biphenyltetracarboxylic acid dianhydride, benzophenonetetracarboxylic acid dianhydride, pyromellitic dianhydride, cyclobutanetetracarboxylic acid dianhydride, perylenetetracarboxylic acid dianhydride, tetrahydrofurantetracarboxylic acid dianhydride, and tetrahydrophthalic anhydride; a glycol compound such as ethylene glycol, propylene glycol, and polyethylene glycol; an alcohol compound such as methanol, ethanol, propanol, n-butanol, cyclohexanol, and benzylalcohol; a solvent-based compound such as propylene glycol methylethylacetate, and N-methylpyrrolidone; a phosphorus compound such as triphenylphosphine; and an amine or ammonium salt compound such as tetramethylammonium chloride, tetraethylammonium bromide, benzyldiethylamine, triethylamine, tributylamine, benzyltriethylammonium chloride.

When the cardo binder resin is used with the acryl binder resin, a photosensitive resin composition having an excellent close-contacting force, a high resolution, and high luminescence characteristics may be obtained.

The cardo binder resin may have a weight average molecular weight of about 500 g/mol to about 50,000 g/mol, e.g., about 3,000 g/mol to about 30,000 g/mol. When the cardo binder resin has a weight average molecular weight within the ranges, a satisfactory pattern may be formed without a residue during a manufacture of a color filter and without losing a film thickness during development.

The cardo binder resin may have an acid value of, e.g., about 100 mgKOH/g to about 140 mgKOH/g.

The binder resin may be included in an amount of, e.g., about 1 wt % to about 10 wt %, based on the total weight of the photosensitive resin composition. When the binder resin is included within the range, excellent developability and sensitivity may be maintained and an undercut may be prevented.

Photopolymerizable Compound

The photopolymerizable compound may be a mono-functional or multi-functional ester of (meth)acrylic acid including at least one ethylenic unsaturated double bond.

The photopolymerizable compound may facilitate sufficient polymerization during exposure in a pattern-forming process and may form a pattern having excellent heat resistance, light resistance, and chemical resistance due to the ethylenic unsaturated double bond.

Examples of the photopolymerizable compound may include ethylene glycol di(meth)acrylate, diethylene glycol di(meth)acrylate, triethylene glycol di(meth)acrylate, propylene glycol di(meth)acrylate, neopentyl glycol di(meth)acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth)acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolacepoxy (meth)acrylate, and the like.

Commercially available examples of the photopolymerizable compound may be as follows. The mono-functional (meth)acrylic acid ester may include Aronix M-101®, M-111®, M-114® (Toagosei Chemistry Industry Co., Ltd.); KAYARAD TC-110S®, TC-120S® (Nippon Kayaku Co., Ltd.); V-158®, V-2311® (Osaka Organic Chemical Ind., Ltd.), and the like. Examples of a difunctional (meth)acrylic acid ester may include Aronix M-210®, M-240®, M-6200® (Toagosei Chemistry Industry Co., Ltd.), KAYARAD HDDA®, HX-220®, R-604® (Nippon Kayaku Co., Ltd.), V-260®, V-312®, V-335 HP® (Osaka Organic Chemical Ind., Ltd.), and the like. Examples of a tri-functional (meth)acrylic acid ester may include Aronix M-309®, M-400®, M-405®, M-450®, M-7100®, M-8030®, M-8060® (Toagosei Chemistry Industry Co., Ltd.), KAYARAD TMPTA®, DPCA-20®, DPCA-30®, DPCA-60®, DPCA-120® (Nippon Kayaku Co., Ltd.), V-295®, V-300®, V-360®, V-GPT®, V-3PA®, V-400® (Osaka Yuki Kayaku Kogyo Co. Ltd.), and the like. These may be used alone or as a mixture of two or more.

The photopolymerizable compound may be treated with acid anhydride to improve developability.

The photopolymerizable compound may be included in an amount of, e.g., about 1 wt % to about 10 wt %, based on the total weight of the photosensitive resin composition. When the photopolymerizable compound is included within the range, the photopolymerizable compound may be sufficiently cured during exposure in a pattern-forming process and has excellent reliability and thus, may form a pattern having excellent heat resistance, light resistance, and chemical resistance and also, excellent resolution and close-contacting properties.

Photopolymerization Initiator

The photopolymerization initiator may be a suitable photopolymerization initiator for a photosensitive resin composition, e.g., an acetophenone compound, a benzophenone compound, a thioxanthone compound, a benzoin compound, an oxime compound, or the like.

Examples of the acetophenone compound may include 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like.

Examples of the benzophenone compound may include benzophenone, benzoyl benzoate, methyl benzoyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like.

Examples of the thioxanthone compound may include thioxanthone, 2-methylthioxanthone, isopropyl thioxanthone, 2,4-diethyl thioxanthone, 2,4-diisopropyl thioxanthone, 2-chlorothioxanthone, and the like.

Examples of the benzoin compound may include benzoin, benzoin methyl ether, benzoin ethyl ether, benzoin isopropyl ether, benzoin isobutyl ether, benzyldimethylketal, and the like.

Examples of the triazine compound may include 2,4,6-trichloro-s-triazine, 2-phenyl 4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like.

Examples of the oxime compound may include an O-acyloxime compound, 2-(O-benzoyloxime)-1-[4-(phenylthio)phenyl]-1,2-octandione, 1-(O-acetyloxime)-1-[9-ethyl-6-(2-methylbenzoyl)-9H-carbazol-3-yl]ethanone, O-ethoxycarbonyl-α-oxyamino-1-phenylpropan-1-one, and the like. Specific examples of the O-acyloxime compound may include 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione 2-oxime-O-benzoate, 1-(4-phenylsulfanyl phenyl)-octan-1-one oxime-O-acetate, 1-(4-phenylsulfanyl phenyl)-butan-1-one oxime-O-acetate, and the like.

In an implementation, the photopolymerization initiator may further include, e.g., a carbazole compound, a diketone compound, a sulfonium borate compound, a diazo compound, an imidazole compound, a biimidazole compound, a fluorene compound, and the like.

The photopolymerization initiator may be used with a photosensitizer capable of causing a chemical reaction by absorbing light and becoming excited and then, transferring its energy.

Examples of the photosensitizer may include tetraethylene glycol bis-3-mercapto propionate, pentaerythritol tetrakis-3-mercapto propionate, dipentaerythritol tetrakis-3-mercapto propionate, and the like.

The photopolymerization initiator may be included in an amount of about 0.01 wt % to about 5 wt %, based on the total weight of the photosensitive resin composition. When the photopolymerization initiator is included within the range, excellent reliability may be secured due to sufficiently curing during exposure in a pattern-forming process, a pattern may have excellent resolution and close-contacting properties as well as excellent heat resistance, light resistance, and chemical resistance, and transmittance may be prevented from deterioration due to a non-reaction initiator.

Solvent

The solvent is a material having compatibility with the compound according to an embodiment, the pigment, the binder resin, the photopolymerizable compound, and the photopolymerization initiator but not reacting therewith.

Examples of the solvent may include alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like. Additionally, high boiling point solvent such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like may be also used.

Considering miscibility and reactivity, ketones such as cyclohexanone, and the like, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol methylether acetate, propylene glycol propylether acetate, and the like may be preferably used.

The solvent may be used in a balance amount, e.g., about 30 wt % to about 70 wt %, based on the total weight of the photosensitive resin composition. When the solvent is included within the ranges, coating properties of the photosensitive resin composition are improved and a film having improved flatness may be obtained.

Other Additives

In an implementation, the photosensitive resin composition may further include an additive, e.g., malonic acid; 3-amino-1,2-propanediol; a silane coupling agent having a reactive substituent such as a carboxyl group, a methacryloyl group, an isocyanate group, an epoxy group, and the like; a leveling agent; a fluorine-based surfactant; a radical polymerization initiator, and the like in order to help prevent stains or spots during the coating, to adjust leveling, or to help prevent pattern residue due to non-development.

Examples of the silane coupling agent may include trimethoxysilyl benzoic acid, γ-methacryl oxypropyl trimethoxysilane, vinyl triacetoxysilane, vinyl trimethoxysilane, γ-iso cyanate propyl triethoxysilane, γ-glycidoxy propyl trimethoxysilane, β-(3,4-epoxycyclohexyl)ethyltrimethoxysilane, and the like. These may be used alone or in a mixture of two or more.

The silane coupling agent may be included in an amount of about 0.01 parts by weight to about 10 parts by weight, based on 100 parts by weight of the photosensitive resin composition. When the silane coupling agent is included within the range, close-contacting properties, storing properties, and the like may be improved.

The photosensitive resin composition may further include an epoxy compound in order to help improve close-contacting properties with a substrate.

Examples of the epoxy compound may include a phenol novolac epoxy compound, a tetramethyl biphenyl epoxy compound, a bisphenol A epoxy compound, an alicyclic epoxy compound, or a combination thereof.

The epoxy compound may be included in an amount of about 0.01 parts by weight to about 20 parts by weight, e.g., about 0.1 parts by weight to about 10 parts by weight, based on 100 parts by weight of the photosensitive resin composition. When the epoxy compound is included within the ranges, close-contacting properties, storage properties, and the like may be improved.

In addition, the photosensitive resin composition may further include a surfactant in order to help improve coating properties and prevent a defect if necessary.

In an implementation, the surfactant may be a fluorine surfactant, and examples of the fluorine surfactant may include, e.g., F-482, F-484, F-478, F-554, and the like of DIC Co., Ltd.

The surfactant may be used in an amount of about 0.001 parts by weight to about 5 parts by weight, based on 100 parts by weight of the photosensitive resin composition. When the surfactant is included within the ranges, excellent wetting on a glass substrate as well as coating uniformity may be secured, but a stain may not be produced.

In an implementation, the photosensitive resin composition may include other additives such as an antioxidant, a stabilizer, and the like in a predetermined amount unless they deteriorate properties of the photosensitive resin composition.

According to another embodiment, a color filter manufactured using the photosensitive resin composition is provided.

A pattern-forming process in the color filter may be as follows.

The process may include coating the positive photosensitive resin composition on a support substrate in a method of spin coating, slit coating, inkjet printing, and the like; drying the coated positive photosensitive resin composition to form a photosensitive resin composition film; exposing the positive photosensitive resin composition film to light; developing the exposed positive photosensitive resin composition film in an alkali aqueous solution to obtain a photosensitive resin film; and heat-treating the photosensitive resin film. Conditions for the patterning process are well known in a related art and will not be illustrated in detail in the specification.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Synthesis of Compounds)

Synthesis Example 1: Synthesis of Compound Represented by Chemical Formula 7

56 g of 2-propanol and 2.9 g of diethylamine were added to 8.1 g of 3',6'-dichlorospiro[3H-2,1-benzoxathiol-3,9'-[9H]xanthene]-1,1-dioxide, and the mixture was stirred at ambient temperature for 3 hours. A precipitate was obtained by using ether and dried to obtain Intermediate 1. 0.5 equivalent of N,N'-dimethyl-1,6-hexanediamine and water were added to Intermediate 1 and then, reacted therewith at 80° C. for one day to obtain the compound represented by Chemical Formula 7 with a total yield of 47%.

[Chemical Formula 7]

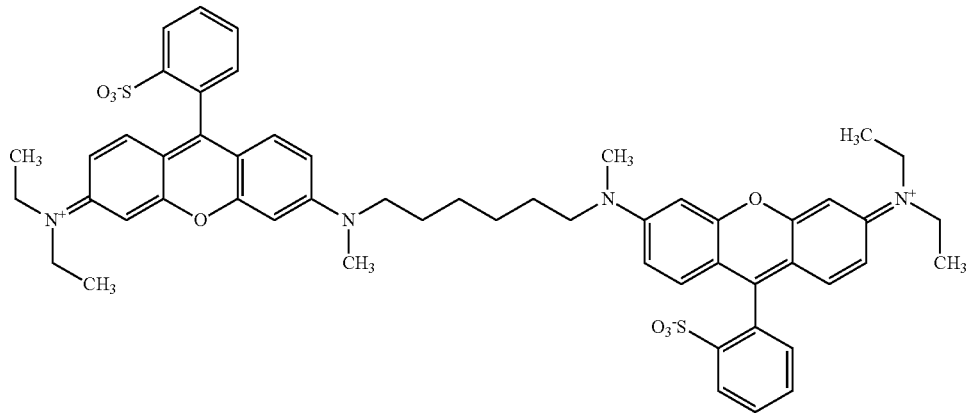

MALDI-TOF MS: 954 m/z

Synthesis Example 2: Synthesis of Compound Represented by Chemical Formula 8

The compound represented by Chemical Formula 8 was obtained according to the same method as Synthesis Example 1 except for using N,N'-diethyl-1,6-hexanediamine instead of N,N'-dimethyl-1,6-hexanediamine in the reaction of Synthesis Example 1.

[Chemical Formula 8]

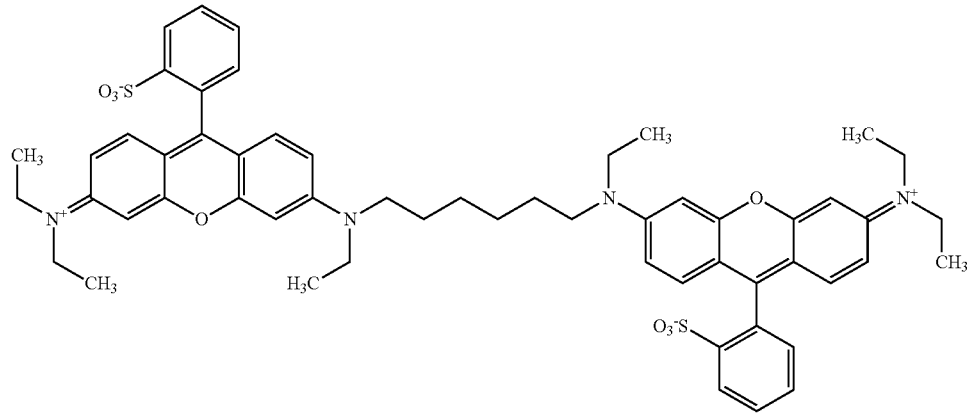

MALDI-TOF MS: 982 m/z

Synthesis Example 3: Synthesis of Compound Represented by Chemical Formula 9

Intermediate 2 was obtained according to the same method as Synthesis Example 1 except for using 2-(ethylamino)ethanol instead of N,N'-dimethyl-1,6-hexanediamine of Synthesis Example 1. The compound represented by Chemical Formula 9 was obtained by using dibutyltin dilaurate and 1,6-diisocyanatohexane in a catalyst amount with Intermediate 2.

[Chemical Formula 9]

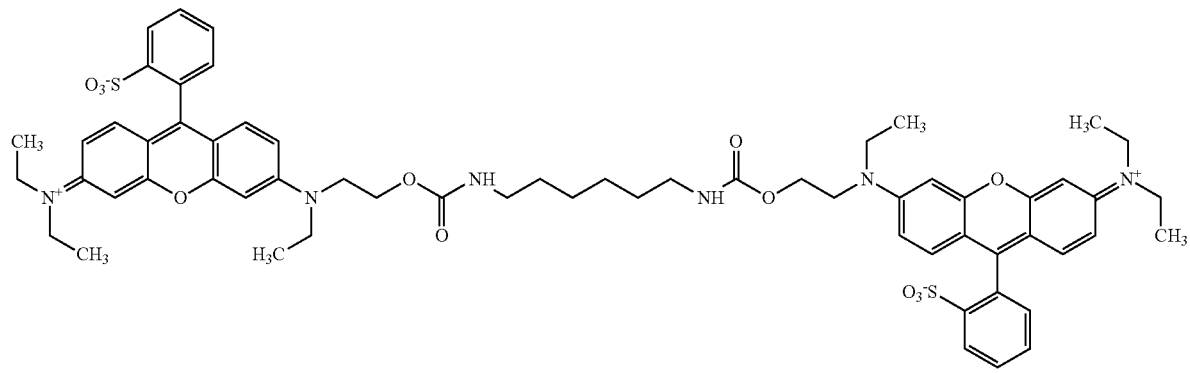

MALDI-TOF MS: 1156 m/z

Synthesis Example 4: Synthesis of Compound Represented by Chemical Formula 10

The compound represented by Chemical Formula 10 was obtained according to the same method as Synthesis Example 3 except for using suberoyl chloride instead of 1,6-diisocyanatohexane of Synthesis Example 3.

[Chemical Formula 10]

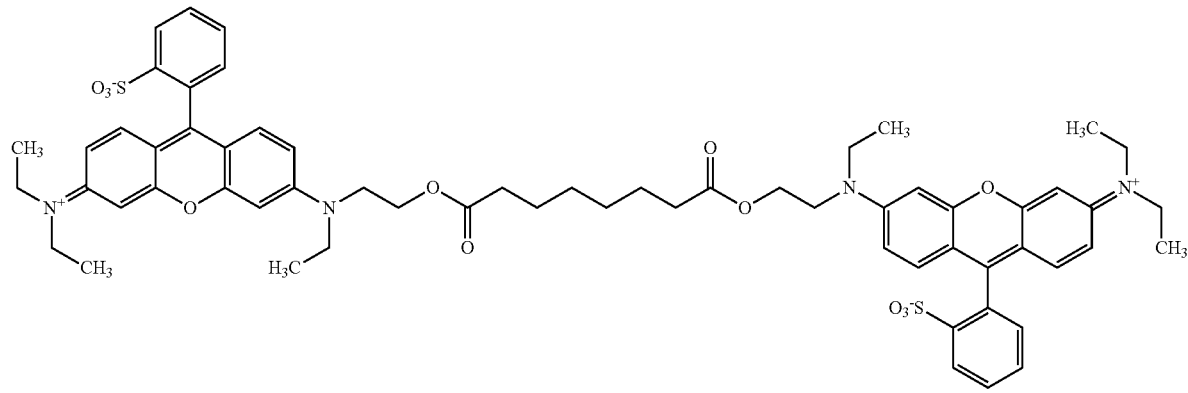

MALDI-TOF MS: 1126 m/z

Synthesis Example 5: Synthesis of Compound Represented by Chemical Formula 11

The compound represented by Chemical Formula 11 was obtained according to the same method as Synthesis Example 3 except for using 1,3-bis(isocyanatomethyl)-cyclohexane instead of 1,6-diisocyanatohexane of Synthesis Example 3.

[Chemical Formula 11]

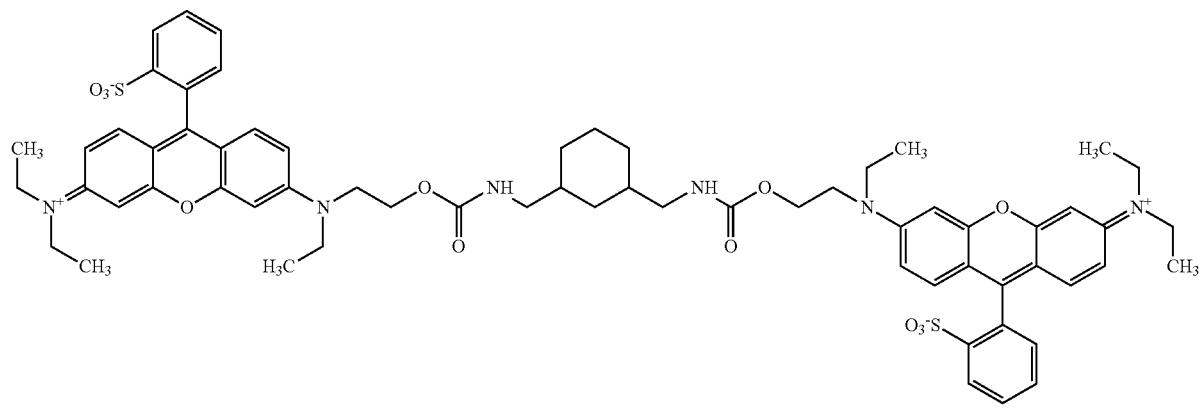

MALDI-TOF MS: 1182 m/z

Synthesis Example 6: Synthesis of Compound Represented by Chemical Formula 12

The compound represented by Chemical Formula 12 was obtained by adding an excess of thionyl chloride to the compound of Chemical Formula 7 in Synthesis Example 1 and refluxing the mixture to substitute sulfoyl chloride for sulfonic acid of an anion moiety and then, reacting the resultant with 2 equivalents of trifluoromethanesulfonamide.

[Chemical Formula 12]

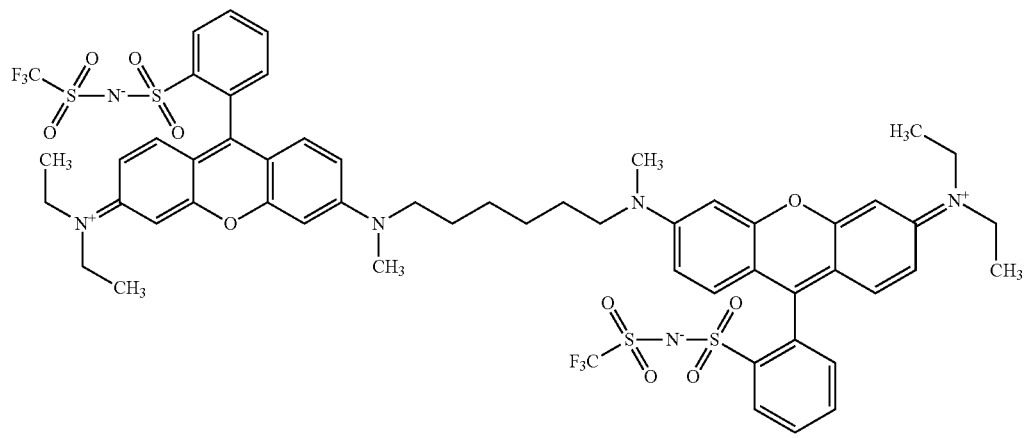

MALDI-TOF MS: 1216 m/z

Synthesis Example 7: Synthesis of Compound Represented by Chemical Formula 13

The compound represented by Chemical Formula 13 was obtained by reacting the compound obtained according to the same method as Synthesis Example 1 with isocyanatoethyl methacrylate in a chloroform solvent except for using 2-(ethylamino)ethanol instead of diethylamine as a starting material.

[Chemical Formula 13]

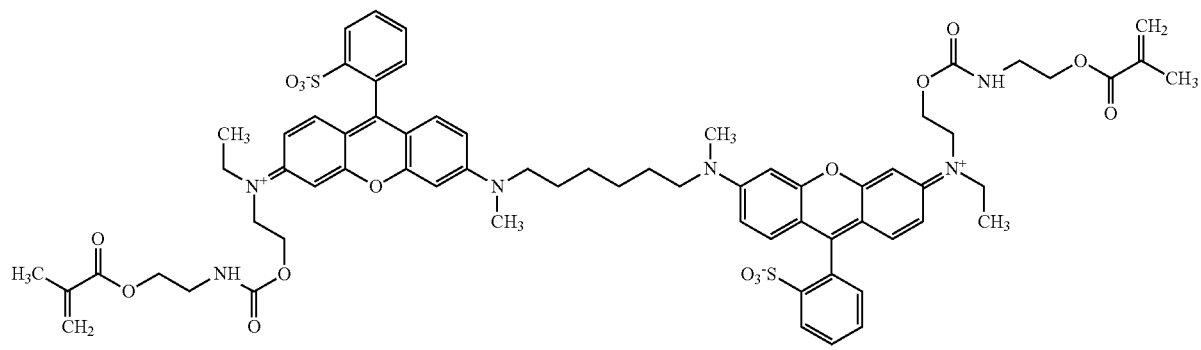

MALDI-TOF MS: 1296 m/z

Synthesis Example 8: Synthesis of Compound Represented by Chemical Formula 14

The compound represented by Chemical Formula 14 was obtained by reacting the compound obtained through the same reaction as Synthesis Example 2 with isocyanatoethyl methacrylate in a chloroform solvent except for using 2-(ethylamino)ethanol instead of diethylamine.

[Chemical Formula 14]

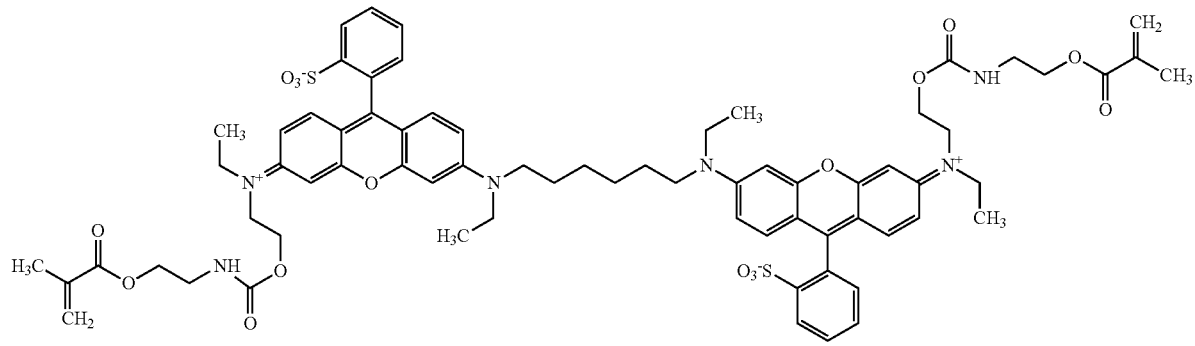

MALDI-TOF MS: 1325 m/z

Synthesis Example 9: Synthesis of Compound Represented by Chemical Formula 15

The compound represented by Chemical Formula 15 was obtained according to the same method as Synthesis Example 1 except for using 1,4,7-trimethyldiethylenetriamine instead of N,N'-dimethyl-1,6-hexanediamine.

[Chemical Formula 15]

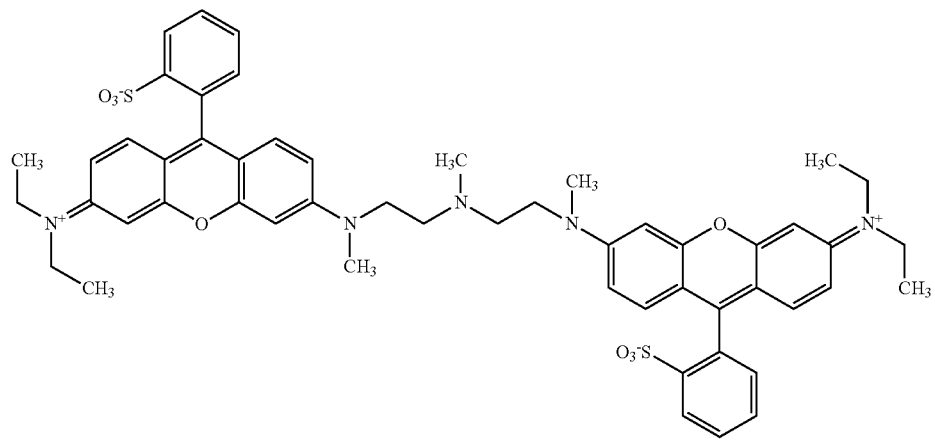

MALDI-TOF MS: 907 m/z

Synthesis Example 10: Synthesis of Compound Represented by Chemical Formula 16

The compound represented by Chemical Formula 16 was obtained according to the same method as Synthesis Example 3 except for using dicyclohexylmethane-4,4'-diisocyanate instead of 1,6-diisocyanatohexane.

[Chemical Formula 16]

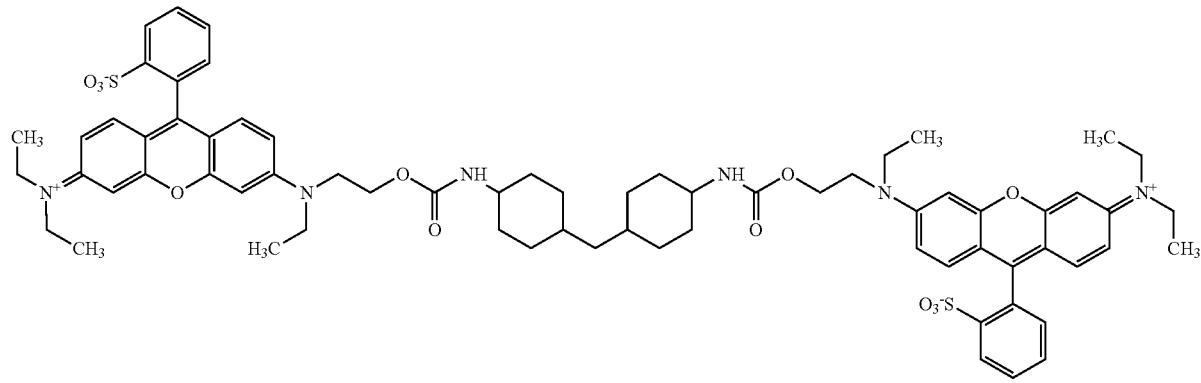

MALDI-TOF MS: 1251 m/z

Synthesis Example 11: Synthesis of Compound Represented by Chemical Formula 17

The compound represented by Chemical Formula 17 was obtained according to the same method as Synthesis Example 8 except for using acryloyl chloride instead of isocyanatoethyl methacrylate.

[Chemical Formula 17]

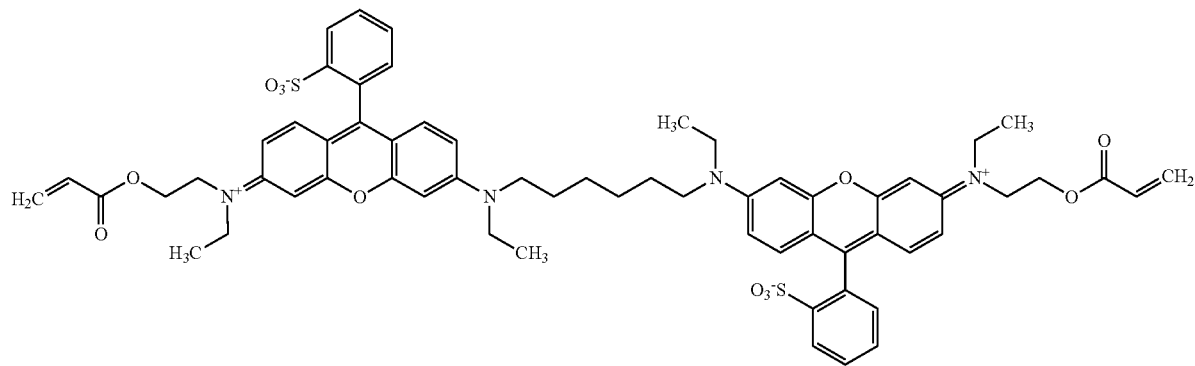

MALDI-TOF MS: 1122 m/z

Synthesis Example 12: Synthesis of Compound Represented by Chemical Formula 18

The compound represented by Chemical Formula 18 was obtained according to the same method as Synthesis Example 8 except for using methacryloyl chloride instead of isocyanatoethyl methacrylate.

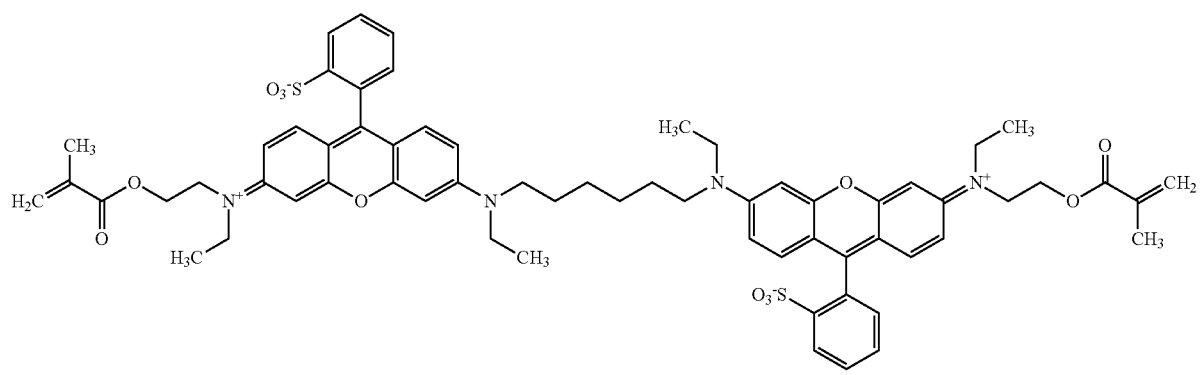

MALDI-TOF MS: 1151 m/z

Synthesis Example 13: Synthesis of Compound Represented by Chemical Formula 19

56 g of 2-propanol and 1.46 g of diethylamine were added to 8.1 g of 3',6'-dichlorospiro[3H-2,1-benzoxathiol-3,9'-[9H]xanthene]-1,1-dioxide, and the mixture was stirred at ambient temperature for 3 hours. A precipitate was obtained by using ether and then, dried to obtain Intermediate 1.

56 g of 2-propanol and 1.78 g of 2-(ethylamino)ethanol were added to 8.1 g of 3',6'-dichlorospiro[3H-2,1-benzoxathiol-3,9'-[9H]xanthene]-1,1-dioxide, and the mixture was stirred at ambient temperature for 3 hours. A precipitate was obtained by using ether and then, dried to obtain Intermediate 2.

Intermediate 1 and Intermediate 2 in each amount of 1 equivalent were mixed, the mixture was reacted with 1 equivalent of N,N'-diethyl-1,6-hexanediamine, and a compound obtained therefrom was reacted with acryloyl chloride to obtain the compound represented by Chemical Formula 19.

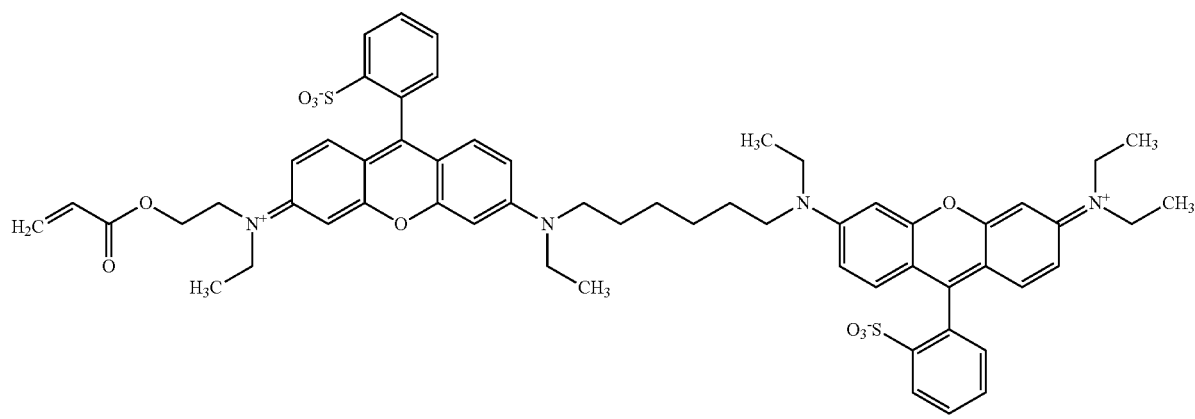

MALDI-TOF MS: 1053 m/z

Synthesis Example 14: Synthesis of Compound Represented by Chemical Formula 20

The compound represented by Chemical Formula 20 was obtained according to the same method as Synthesis Example 13 except for using methacryloyl chloride instead of acryloyl chloride.

[Chemical Formula 20]

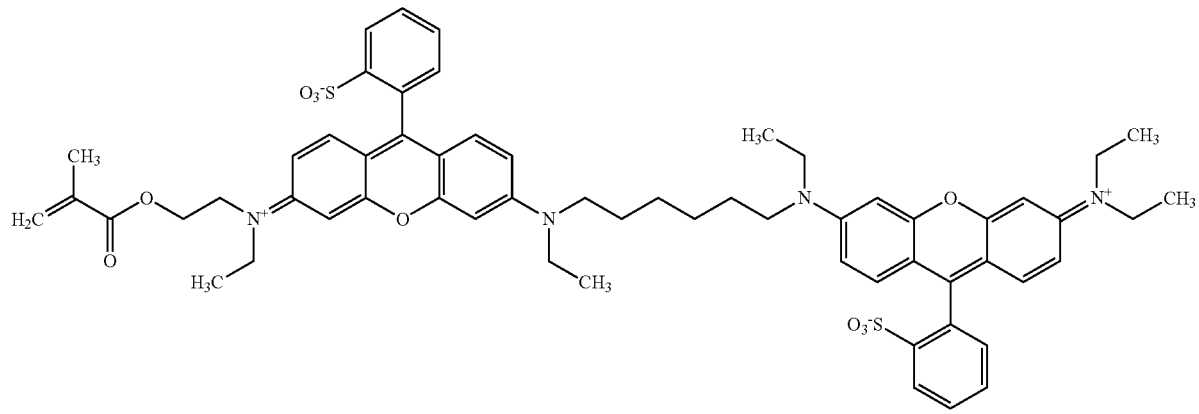

MALDI-TOF MS: 1067 m/z

Synthesis Example 15: Synthesis of Compound Represented by Chemical Formula 21

The compound represented by Chemical Formula 21 was obtained according to the same method as Synthesis Example 13 except for using isocyanatoethyl methacrylate instead of acryloyl chloride.

[Chemical Formula 21]

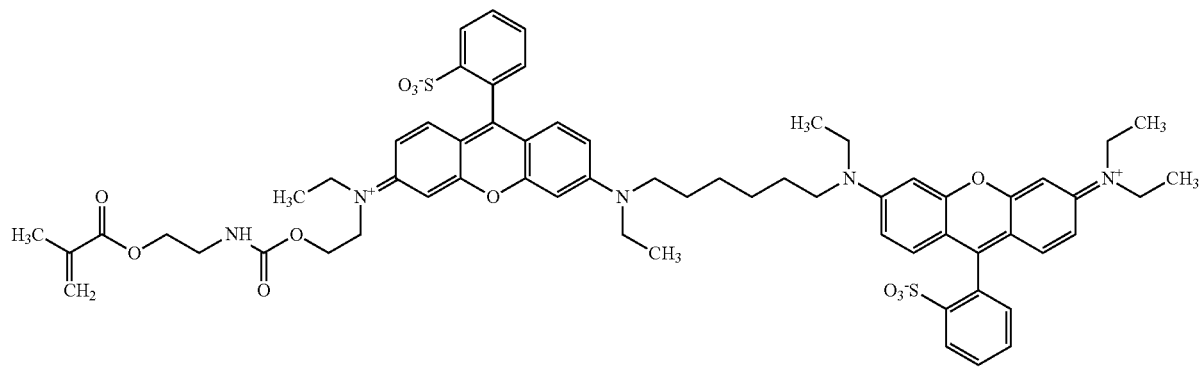

MALDI-TOF MS: 1154 m/z

Comparative Synthesis Example 1: Synthesis of Compound Represented by Chemical Formula X

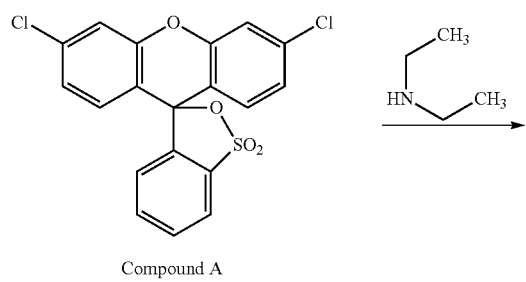

Compound A

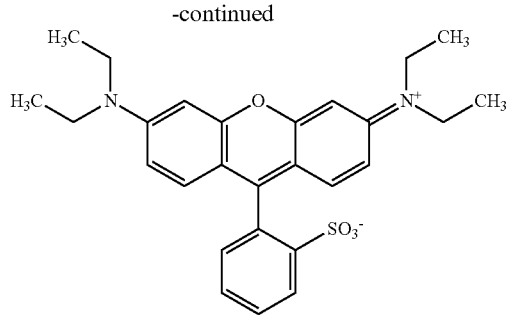

Chemical Formula X 10 g of Compound A (CAS No. 77545-45-0) was put in a reactor and dissolved in 100 g of 2-propanol. 7.2 g of diethylamine was added thereto, and the mixture was stirred at 80° C. for 8 hours. The reactant was cooled down, and 800 mL of water was added thereto to produce a precipitate. The precipitate was suction-filtered and additionally washed with water. A product filtered therefrom was dried to obtain 9.9 g of the compound represented by Chemical Formula X (a yield of 84%).

MALDI-TOF MS: 478.2 m/z

Evaluation 1: Solubility 0.5 g of each compound represented by Chemical Formula 7 to Chemical Formula 21 and Chemical Formula X was respectively added to diluting solvents (MeOH, $CH_2Cl_2$, cyclohexanone), each solution was stirred with a rotary mixer (Mixrotar VMR-5, Iuchi Seieido Co., Ltd.) at 25° C. and 100 rpm for 1 hour, and then, the dissolution state of each compound (the amount of the compound dissolved in the solvents) was examined, and the results are shown in Table 1.

Solubility Evaluation Reference
X: solubility of less than 1 wt %
○: solubility of greater than or equal to 1 wt % and less than 5 wt %
◎: solubility of greater than or equal to 5 wt %

TABLE 1

|  | Amount of dissolved compound (wt %) | |
| --- | --- | --- |
|  | Chloroform | Diacetone alcohol |
| Chemical Formula 7 | ○ | ○ |
| Chemical Formula 8 | ○ | ○ |
| Chemical Formula 9 | ○ | ○ |
| Chemical Formula 10 | ○ | ○ |
| Chemical Formula 11 | ○ | ○ |
| Chemical Formula 12 | ○ | ○ |
| Chemical Formula 13 | ◎ | ◎ |
| Chemical Formula 14 | ◎ | ◎ |

TABLE 1-continued

|  | Amount of dissolved compound (wt %) | |
| --- | --- | --- |
|  | Chloroform | Diacetone alcohol |
| Chemical Formula 15 | ○ | ○ |
| Chemical Formula 16 | ○ | ○ |
| Chemical Formula 17 | ◎ | ◎ |
| Chemical Formula 18 | ◎ | ◎ |
| Chemical Formula 19 | ◎ | ◎ |
| Chemical Formula 20 | ◎ | ◎ |
| Chemical Formula 21 | ◎ | ◎ |
| Chemical Formula X | X | X |

Solubility Evaluation Reference
X: solubility of less than 1 wt %
○: solubility of greater than or equal to 1 wt % and less than 5 wt %
◎: solubility of greater than or equal to 5 wt %

(Synthesis of Photosensitive Resin Composition)

Example 1

Photosensitive resin compositions according to Example 1 to Example 13, Comparative Example 1 to Comparative Example 3, Reference Example 1, and Reference Example 2 were prepared by mixing the following components to have compositions shown in Table 2 to Table 4.

Specifically, a photopolymerization initiator was dissolved in a solvent, the solution was stirred at ambient temperature for 2 hours, a binder resin and a photopolymerizable compound were added thereto, and the mixture was stirred at ambient temperature for 2 hours. Subsequently, the compound represented by Chemical Formula 5 and a pigment (a pigment dispersion liquid) as a colorant were added to the reactant, and the mixture was stirred at ambient temperature for one hour. Then, each product therefrom was filtered three times to remove impurities to prepare photosensitive resin compositions.

TABLE 2

(unit: wt %)

|  |  | Example 1 | Example 2 | Example 3 | Example 4 | v 5 | Example 6 |
| --- | --- | --- | --- | --- | --- | --- | --- |
| (A) Binder resin |  | 5.0 | 5.0 | 5.0 | 5.0 | 5.0 | 5.0 |
| (B) Colorant | B-1 | 6.0 | — | — | — | — | — |
|  | B-2 | — | 6.0 | — | — | — | — |
|  | B-3 | — | — | 6.0 | — | — | — |
|  | B-4 | — | — | — | 6.0 | — | — |
|  | B-5 | — | — | — | — | 6.0 | — |
|  | B-6 | — | — | — | — | — | 6.0 |
|  | B-7 | — | — | — | — | — | — |
|  | B-8 | — | — | — | — | — | — |
|  | B-9 | — | — | — | — | — | — |
|  | B-10 | — | — | — | — | — | — |
|  | B-11 | — | — | — | — | — | — |
|  | B-12 | — | — | — | — | — | — |
|  | B-13 | 49.0 | 49.0 | 49.0 | 49.0 | 49.0 | 49.0 |
| (C) Photopolymerizable compound |  | 3.1 | 3.1 | 3.1 | 3.1 | 3.1 | 3.1 |
| (D) Photopolymerization initiator |  | 0.5 | 0.5 | 0.5 | 0.5 | 0.5 | 0.5 |
| (E) Solvent |  | 36.2 | 36.2 | 36.2 | 36.2 | 36.2 | 36.2 |
| (F) Other additive |  | 0.2 | 0.2 | 0.2 | 0.2 | 0.2 | 0.2 |
| Total |  | 100.0 | 100.0 | 100.0 | 100.0 | 100.0 | 100.0 |

TABLE 3

(unit: wt %)

|  |  | Example 7 | Example 8 | Example 9 | Example 10 | Example 11 |
|---|---|---|---|---|---|---|
| (A) Binder resin | | 5.0 | 5.0 | 5.0 | 5.0 | 8.0 |
| (B) Colorant | B-1 | — | — | — | — | — |
| | B-2 | — | — | — | — | 8.0 |
| | B-3 | — | — | — | — | — |
| | B-4 | — | — | — | — | — |
| | B-5 | — | — | — | — | — |
| | B-6 | — | — | — | — | — |
| | B-7 | 6.0 | — | — | — | — |
| | B-8 | — | 6.0 | — | — | — |
| | B-9 | — | — | 6.0 | — | — |
| | B-10 | — | — | — | 6.0 | — |
| | B-11 | — | — | — | — | — |
| | B-12 | — | — | — | — | — |
| | B-13 | 49.0 | 49.0 | 49.0 | 49.0 | 49.0 |
| (C) Photopolymerizable compound | | 3.1 | 3.1 | 3.1 | 3.1 | 3.1 |
| (D) Photopolymerization initiator | | 0.5 | 0.5 | 0.5 | 0.5 | 0.5 |
| (E) Solvent | | 36.2 | 36.2 | 36.2 | 36.2 | 34.2 |
| (F) Other additive | | 0.2 | 0.2 | 0.2 | 0.2 | 0.2 |
| Total | | 100.0 | 100.0 | 100.0 | 100.0 | 100.0 |

TABLE 4

(unit: wt %)

|  |  | Comparative Example 1 | Comparative Example 2 | Reference Example 1 | Reference Example 2 |
|---|---|---|---|---|---|
| (A) Binder resin | | 5.0 | 5.0 | 5.0 | 5.0 |
| (B) Colorant | B-1 | — | — | — | — |
| | B-2 | — | — | 4.0 | 12.0 |
| | B-3 | — | — | — | — |
| | B-4 | — | — | — | — |
| | B-5 | — | — | — | — |
| | B-6 | — | — | — | — |
| | B-7 | — | — | — | — |
| | B-8 | — | — | — | — |
| | B-9 | — | — | — | — |
| | B-10 | — | — | — | — |
| | B-11 | 12.26 | — | — | — |
| | B-12 | — | 8.8 | — | — |
| | B-13 | 47.03 | 50.5 | 49.0 | 49.0 |
| (C) Photopolymerizable compound | | 3.1 | 3.1 | 3.1 | 3.1 |
| (D) Photopolymerization initiator | | 0.5 | 0.5 | 0.5 | 0.5 |
| (E) Solvent | | 34.01 | 33.2 | 38.2 | 30.2 |
| (F) Other additive | | 0.2 | 0.2 | 0.2 | 0.2 |
| Total | | 100.0 | 100.0 | 100.0 | 100.0 |

(A) Binder Resin Acryl-based binder resin (methacrylic acid/benzylmethacrylate = 15/85 (w/w), weight average molecular weight = 22,000 g/mol, acid value = 100 mgKOH/g), Samsung SDI Co., Ltd.)
(B) Colorant
(B-1) Compound of Synthesis Example 1
(B-2) Compound of Synthesis Example 2
(B-3) Compound of Synthesis Example 3
(B-4) Compound of Synthesis Example 4
(B-5) Compound of Synthesis Example 5
(B-6) Compound of Synthesis Example 6
(B-7) Compound of Synthesis Example 7
(B-8) Compound of Synthesis Example 8
(B-9) Compound of Synthesis Example 9
(B-10) Compound of Synthesis Example 10
(B-11) Xanthene compound dispersion liquid, RCP-24 (Wako Ltd.)
(B-12) Compound of Comparative Synthesis Example 1
(B-13) Pigment Red 254 dispersion liquid (Sanyo Co., Ltd.)
(C) Photopolymerizable Compound dipentaerythritol hexaacrylate (DPHA, Sartomer)
(D) Photopolymerization Initiator OXE-01 (BASF)
(E) Solvent Propylene glycol monomethylether acetate (PGMEA, Sigma-Aldrich)
(F) Additive F-554 (10% diluted solution) (DIC Co., Ltd.)

Example 12

The photosensitive resin composition according to Example 12 was prepared by mixing the following components to have a composition shown in Table 5 according to same method as in Example 1.

TABLE 5

(unit: wt %)

| | | Materials | Amounts |
|---|---|---|---|
| Colorant | Dye | Compound of Synthesis Example 7 (compound represented by Chemical Formula 13) | 5.0 |
| | Pigment dispersion liquid | Pigment Y138 pigment dispersion | 15.0 |
| | Binder resin | (A)/(B) = 15/85 (w/w), molecular weight (Mw) = 22,000 g/mol (A): methacrylic acid (B): benzylmethacrylate | 3.5 |
| | Photopolymerizable compound | Dipentaerythritolhexaacrylate (DPHA) | 8.0 |
| | Photopolymerization initiator | 1,2-octandione | 1.0 |
| | | 2-dimethylamino-2-(4-methyl-benzyl)-1-(4-morpholin-4-yl-phenyl)-butan-1-one | 0.5 |
| | Solvent | Cyclohexanone | 37.0 |
| | | PGMEA (Propylene Glycol Monomethyl Ether Acetate) | 30.0 |
| | Total | | 100.00 |

Example 13

A photosensitive resin composition was prepared according to the same method as Example 12 except for using the compound of Synthesis Example 8 (the compound represented by Chemical Formula 14) instead of the compound of Synthesis Example 7 (the compound represented by Chemical Formula 13).

Example 14

A photosensitive resin composition was prepared according to the same method as Example 12 except for using the compound of Synthesis Example 11 (the compound represented by Chemical Formula 17) instead of the compound of Synthesis Example 7 (the compound represented by Chemical Formula 13).

Example 15

A photosensitive resin composition was prepared according to the same method as Example 12 except for using the compound of Synthesis Example 12 (the compound represented by Chemical Formula 18) instead of the compound of Synthesis Example 7 (the compound represented by Chemical Formula 13).

Comparative Example 3

A photosensitive resin composition was prepared according to the same method as Example 12 except for using a red pigment (SC-P541-4214, Toyo Corporation) instead of the compound of Synthesis Example 7 (the compound represented by Chemical Formula 13).

Evaluation 2-1: Measurement of Luminance

The photosensitive resin compositions according to Example 1 to Example 11, Comparative Example 1, Comparative Example 2, Reference Example 1, and Reference Example 2 were respectively coated to be 1 μm to 3 μm thick on a 1 mm-thick degreased glass substrate and dried on a 90° C. hot plate for 2 minutes to obtain films. The entire surfaces of the films were exposed by using a high pressure mercury lamp having a main wavelength of 365 nm (50 mJ/cm$^2$). Subsequently, the films were dried (post-baked, PSB) in a 230° C. forced convection drying furnace for 30 minutes to obtain samples. Color coordinates (Rx, Ry) and luminance (Y) of pixel layers were measured by using a spectrophotometer (MCPD3000, Otsuka Electronics Co., Ltd.), and the results are shown in Table 6. The luminance (Y) were calculated with a reference to a color coordinate (Rx).

TABLE 6

| | Step | Rx | Ry | Luminance |
|---|---|---|---|---|
| Example 1 | Before PSB | 0.668 | 0.3267 | 17.98 |
| | After PSB | 0.668 | 0.3261 | 17.56 |
| Example 2 | Before PSB | 0.668 | 0.3256 | 18.13 |
| | After PSB | 0.668 | 0.3243 | 17.72 |
| Example 3 | Before PSB | 0.668 | 0.3265 | 18.01 |
| | After PSB | 0.668 | 0.3257 | 17.40 |
| Example 4 | Before PSB | 0.668 | 0.3257 | 18.12 |
| | After PSB | 0.668 | 0.3251 | 17.57 |
| Example 5 | Before PSB | 0.668 | 0.3260 | 18.08 |
| | After PSB | 0.668 | 0.3250 | 17.62 |
| Example 6 | Before PSB | 0.668 | 0.3272 | 17.91 |
| | After PSB | 0.668 | 0.3259 | 17.60 |
| Example 7 | Before PSB | 0.668 | 0.3262 | 18.05 |
| | After PSB | 0.668 | 0.3254 | 17.54 |

TABLE 6-continued

| | Step | Rx | Ry | Luminance |
|---|---|---|---|---|
| Example 8 | Before PSB | 0.668 | 0.3274 | 17.88 |
| | After PSB | 0.668 | 0.3265 | 17.65 |
| Example 9 | Before PSB | 0.668 | 0.3258 | 18.10 |
| | After PSB | 0.668 | 0.3248 | 17.50 |
| Example 10 | Before PSB | 0.668 | 0.3262 | 18.05 |
| | After PSB | 0.668 | 0.3250 | 17.61 |
| Example 11 | Before PSB | 0.668 | 0.3308 | 18.95 |
| | After PSB | 0.668 | 0.3292 | 18.45 |
| Comparative Example 1 | Before PSB | 0.668 | 0.3265 | 17.42 |
| | After PSB | 0.668 | 0.3266 | 17.29 |
| Comparative Example 2 | Before PSB | 0.668 | 0.3294 | 17.58 |
| | After PSB | 0.668 | 0.3274 | 17.27 |
| Reference Example 1 | Before PSB | 0.668 | 0.3200 | 17.15 |
| | After PSB | 0.668 | 0.3187 | 16.76 |
| Reference Example 2 | Before PSB | 0.668 | 0.3357 | 19.72 |
| | After PSB | 0.668 | 0.3331 | 18.75 |

Evaluation 2-2: Measurement of Luminance

The photosensitive resin compositions according to Example 12 to Example 15 and Comparative Example 3 were respectively coated to be 1 μm to 3 μm thick on a 1 mm-thick degreased glass substrate and dried on a 90° C. hot plate for 2 minutes to obtain films. The films were exposed by using a high pressure mercury lamp having a main wavelength of 365 nm. Subsequently, the films were dried in a 200° C. forced convection drying furnace for 5 minutes to obtain samples. Color coordinates and luminance (Y) of pixel layers were measured by using a spectrophotometer (MCPD3000, Otsuka Electronics Co., Ltd.), and the results are shown in Table 7. The luminance (Y) was calculated with a reference to a color coordinate (Ry).

TABLE 7

| | Luminance (Y) |
|---|---|
| Example 12 | 14.1 |
| Example 13 | 14.3 |
| Example 14 | 14.2 |
| Example 15 | 14.2 |
| Comparative Example 3 | 13.9 |

From Table 7, the photosensitive resin compositions of Example 12 to Example 15 including a compound (dye) represented by Chemical Formula 1 as a colorant exhibited excellent luminance compared with the photosensitive resin composition of Comparative Example 3.

Evaluation 3: Measurement of Heat Resistance

The photosensitive resin compositions according to Example 1 to Example 11, Comparative Example 1, Comparative Example 2, Reference Example 1, and Reference Example 2 were respectively coated to be 1 m to 3 μm thick on a 1 mm-thick degreased glass substrate and dried on a 90° C. hot plate for 2 minutes to obtain films. The entire surfaces of the films were exposed by using a high pressure mercury lamp having a main wavelength of 365 nm (50 mJ/cm$^2$). Subsequently, the films were dried (post-baked, PSB) in a 230° C. forced convection drying furnace for 20 minutes to obtain samples. Heat resistance was measured by calculating del (E*) based on color change values before and after post-baking and the results are shown in Table 8.

TABLE 8

| | Heat resistance (del (E*)) |
|---|---|
| Example 1 | 1.1 |
| Example 2 | 0.7 |
| Example 3 | 1.30 |
| Example 4 | 1.22 |
| Example 5 | 0.81 |
| Example 6 | 0.65 |
| Example 7 | 1.03 |
| Example 8 | 0.77 |
| Example 9 | 1.20 |
| Example 10 | 0.68 |
| Example 11 | 0.75 |
| Comparative Example 1 | 0.35 |
| Comparative Example 2 | 1.5 |
| Reference Example 1 | 0.6 |
| Reference Example 2 | 2.05 |

Evaluation 4: Measurement of Patternability

The photosensitive resin compositions according to Example 1 to Example 11, Comparative Example 1, Comparative Example 2, Reference Example 1, and Reference Example 2 were respectively coated to be 1 m to 3 μm thick on a 1 mm-thick degreased glass substrate and dried on a 90° C. hot plate for 2 minutes to obtain films. The entire surfaces of the films were exposed by using a high pressure mercury lamp having a main wavelength of 365 nm (50 mJ/cm$^2$) and were developed to obtain patterns. The developing solution was prepared by diluting KOH solution manufactured by Hoimyung, and then the time (second) for showing the pattern was monitored. (Herein, BP should be measured to be 25 seconds to 35 seconds which makes it be applied to an actual process easily.) The developed pattern substrate was dried (post-baked, PSB) in a 230° C. forced convection drying furnace for 20 minutes to complete the patterning. The pattern sizes (CD, 100 μm reference) of the patterned samples were measured using an optical microscope X500 and the results are shown in Table 9 and FIGS. 1 and 2. (When measured CDs immediately after post-baking are 102 μm to 104 μm, it may be considered to have appropriate sensitivity.) Pattern tearing was evaluated by an optical microscope as follows.

○: Pattern circumferences and close-contacting forces were good

Δ: Pattern circumferences were torn x: Patterns were delaminated

TABLE 9

| | CD immediately after development (μm) | CD immediately after post-baking (μm) | BP (seconds) | Pattern tearing (close-contacting force) |
|---|---|---|---|---|
| Example 1 | 102.5 | 102.9 | 31 | ○ |
| Example 2 | 102.7 | 103.6 | 30 | ○ |
| Example 3 | 102.6 | 103.1 | 31 | ○ |
| Example 4 | 102.8 | 103.5 | 31 | ○ |
| Example 5 | 102.7 | 103.3 | 32 | ○ |
| Example 6 | 102.3 | 102.8 | 30 | ○ |
| Example 7 | 102.5 | 103.1 | 30 | ○ |
| Example 8 | 102.6 | 103.1 | 31 | ○ |
| Example 9 | 103.0 | 103.5 | 32 | ○ |
| Example 10 | 102.9 | 103.6 | 29 | ○ |
| Example 11 | 102.8 | 103.5 | 31 | ○ |
| Comparative Example 1 | 98.6 | 99.2 | 38 | Δ |
| Comparative Example 2 | 102.1 | 102.3 | 34 | Δ |
| Reference Example 1 | 108.0 | 108.7 | 48 | Δ |
| Reference Example 2 | 97.5 | 98.2 | 28 | X |

○: Pattern circumferences and close-contacting forces were good

Δ: Pattern circumferences were torn

X: Patterns were delaminated

Figure 2:
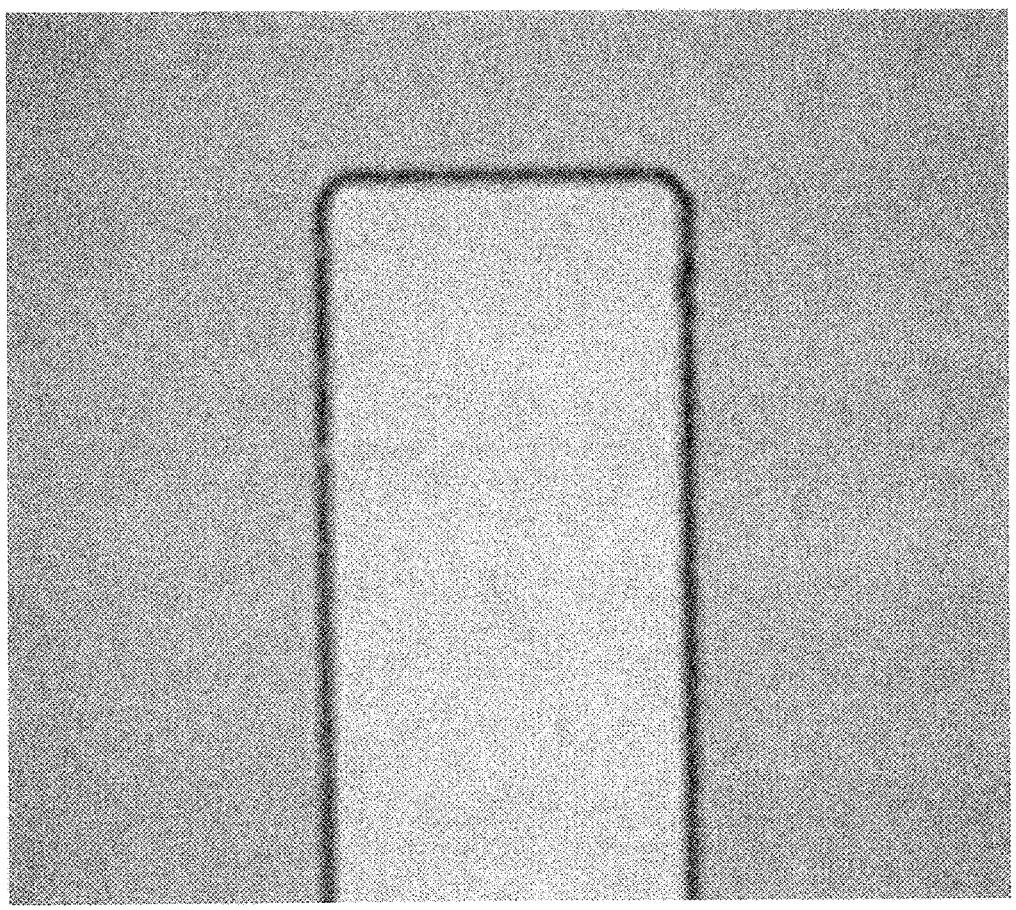
FIG. 2 illustrates a pattern image of the specimen manufactured using the photosensitive resin composition according to Comparative Example 2.

From Tables 6 to 9 and FIGS. 1 and 2, the photosensitive resin compositions of the Examples exhibited excellent luminance, heat resistance, and patternability by including the compound represented by Chemical Formula 1 as a colorant (dye). Particularly, when the compound represented by Chemical Formula 1 was used in an amount of less than 5 wt % based on a total weight of the photosensitive resin composition even if the compound represented by Chemical Formula 1 was used as the colorant (dye), luminance were deteriorated (while heat resistance was improved), and additionally developability and patternability were deteriorated as BP became longer. When the compound represented by Chemical Formula 1 was included in an amount of greater than 10 wt % based on a total amount of the photosensitive resin composition, initial luminance was high but heat resistance was inferior and thus luminance after post-baking was abruptly decreased and further patternability was deteriorated. When the compound represented by Chemical Formula 1 was included in an amount of less than 5 wt % or greater than 10 wt % based on a total weight of the photosensitive resin composition, sensitivity was remarkably deteriorated.

By way of summation and review, a pigment dispersion method of forming a color filter may provide a colored thin film by repeating a series of processes such as coating a photopolymerizable composition including a colorant on a transparent substrate including a black matrix, exposing a formed pattern to light, removing a non-exposed part with a solvent, and thermally curing the same.

A coloring photosensitive resin composition used for manufacturing a color filter according to the pigment dispersion method may include an alkali soluble resin, a photopolymerization monomer, a photopolymerization initiator, a solvent, other additives, and the like, and additionally, an epoxy resin and the like.

The pigment dispersion method may be applied to manufacture an LCD such as a mobile phone, a laptop, a monitor, and TV. In the photosensitive resin composition for a color filter using the pigment dispersion method, there may be difficulties in minutely pulverizing of a powder, requiring various additives for stabilizing a dispersion liquid even if dispersed and complex processes, and further maintaining optimal quality of a pigment dispersion liquid under complicated storage and transportation conditions.

In addition, a color filter manufactured by using a pigment-type photosensitive resin composition may have a limit in luminance and a contrast ratio due to a pigment particle size. A dye may have similar heat resistance and chemical resistance to those of a pigment.

The embodiments may provide a compound having improved solubility in an organic solvent and improved fluorescence quenching properties and spectroscopic coherence by having a form of a dimer linked with a functional linking group.

The compound according to an embodiment may exhibit improved solubility in an organic solvent and improved fluorescence quenching properties and spectroscopic coherence, and thus a photosensitive resin composition including a colorant (dye) including the compound as a constituent element may provide a color filter having improved luminance, contrast ratio, heat resistance, and pattern characteristics.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Chemical Formula 1:

[Chemical Formula 1]

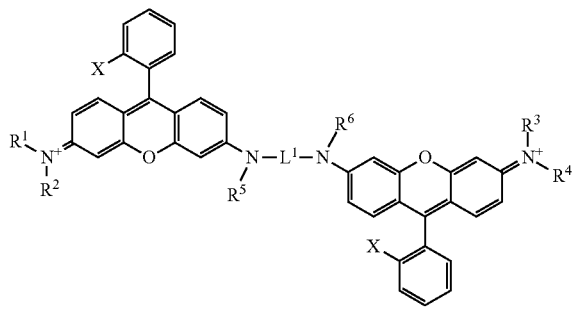

wherein, in Chemical Formula 1,
R$^1$ to R$^6$ are each independently a hydrogen atom or a substituted or unsubstituted C1 to C20 alkyl group,
L$^1$ is a substituted or unsubstituted C1 to C20 alkylene group, a substituted or unsubstituted C3 to C20 cycloalkylene group, *—OC(=O)NH—*, *—O(C=O)—*, *—NR$^X$—*, or a combination thereof, in which R$^x$ is a substituted or unsubstituted C1 to C10 alkyl group, and
X is a group represented by Chemical Formula X-1 or Chemical Formula X-2,

[Chemical Formula X-1]

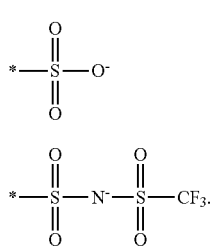

[Chemical Formula X-2]

2. The compound as claimed in claim 1, wherein L$^1$ is a group represented by Chemical Formula 2:

[Chemical Formula 2]

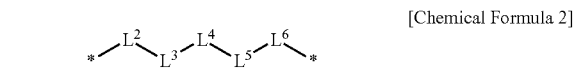

wherein, in Chemical Formula 2, L$^2$ to L$^6$ are each independently a single bond, a substituted or unsubstituted C1 to C10 alkylene group, a substituted or unsubstituted C3 to C20 cycloalkylene group, *—OC(=O)NH—*, *—O(C=O)—* or *—NR$^X$—*, in which R$^x$ is a substituted or unsubstituted C1 to C10 alkyl group, provided that all of L$^2$ to L$^6$ are not a single bond.

3. The compound as claimed in claim 2, wherein the group represented by Chemical Formula 2 is a substituted or unsubstituted C1 to C20 alkylene group.

4. The compound as claimed in claim 2, wherein the group represented by Chemical Formula 2 is a group represented by Chemical Formula 3:

[Chemical Formula 3]

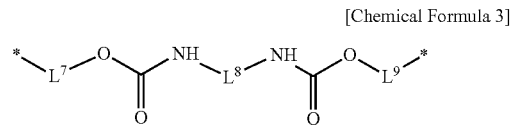

wherein, in Chemical Formula 3, L$^7$ to L$^9$ are each independently a substituted or unsubstituted C1 to C10 alkylene group, a substituted or unsubstituted C3 to C10 cycloalkylene group, or a combination thereof.

5. The compound as claimed in claim 4, wherein L$^7$ to L$^9$ are independently a substituted or unsubstituted C1 to C10 alkylene group or a group represented by Chemical Formula 3-1 or Chemical Formula 3-2:

[Chemical Formula 3-1]

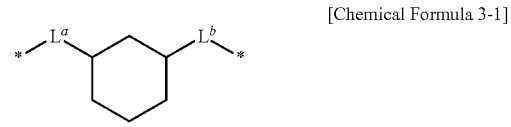

[Chemical Formula 3-2]

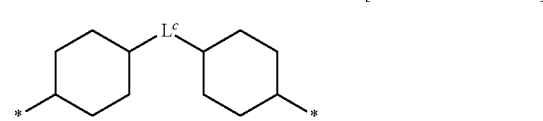

wherein, in Chemical Formula 3-1 and Chemical Formula 3-2, L$^a$ to L$^c$ are each independently a substituted or unsubstituted C1 to C5 alkylene group.

6. The compound as claimed in claim 2, wherein the group represented by Chemical Formula 2 is a group represented by Chemical Formula 4:

[Chemical Formula 4]

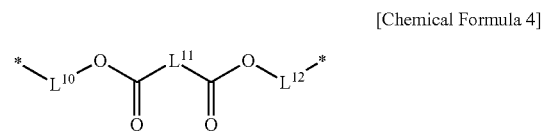

wherein, in Chemical Formula 4, L$^{10}$ to L$^{12}$ are each independently a substituted or unsubstituted C1 to C10 alkylene group.

7. The compound as claimed in claim 2, wherein the group represented by Chemical Formula 2 is a group represented by Chemical Formula 5:

[Chemical Formula 5]

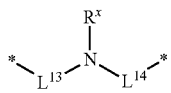

wherein, in Chemical Formula 5,

L$^{13}$ and L$^{14}$ are each independently a substituted or unsubstituted C1 to C10 alkylene group, and R$^x$ is a substituted or unsubstituted C1 to C10 alkyl group.

8. The compound as claimed in claim 1, wherein at least one of R$^1$ to R$^4$ is a group represented by Chemical Formula 6-1 or Chemical Formula 6-2:

[Chemical Formula 6-1]

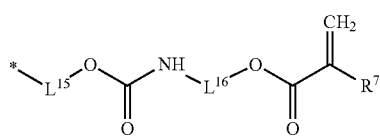

[Chemical Formula 6-2]

wherein, in Chemical Formula 6-1 and Chemical Formula 6-2,

R$^7$ is a hydrogen atom or a substituted or unsubstituted C1 to C10 alkyl group, and L$^{15}$ and L$^{16}$ are each independently a substituted or unsubstituted C1 to C10 alkylene group.

9. The compound as claimed in claim 1, wherein the compound represented by Chemical Formula 1 is represented by one of Chemical Formula 7 to Chemical Formula 21:

[Chemical Formula 7]

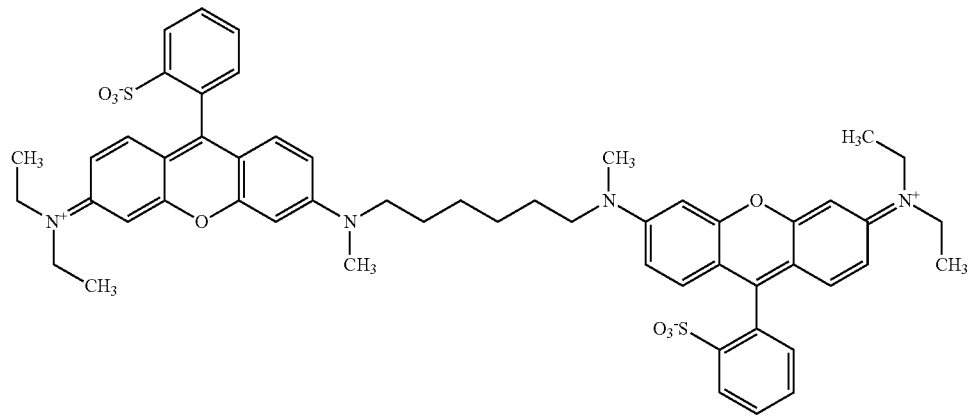

[Chemical Formula 8]

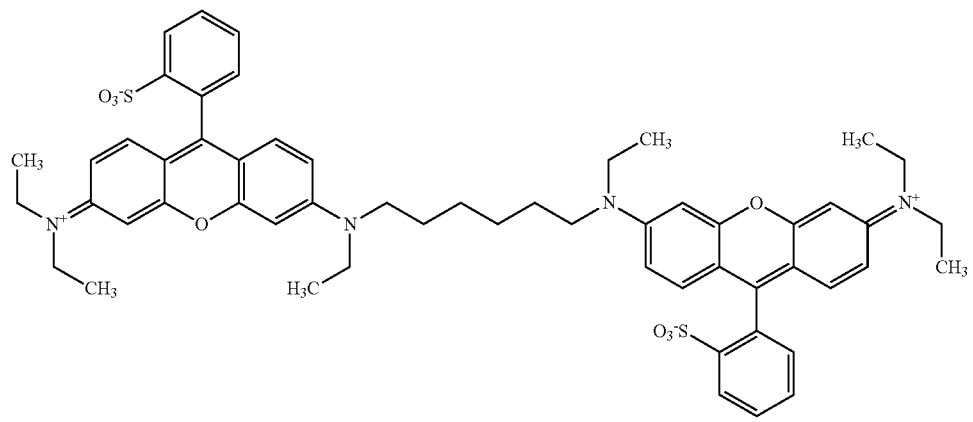

[Chemical Formula 9]
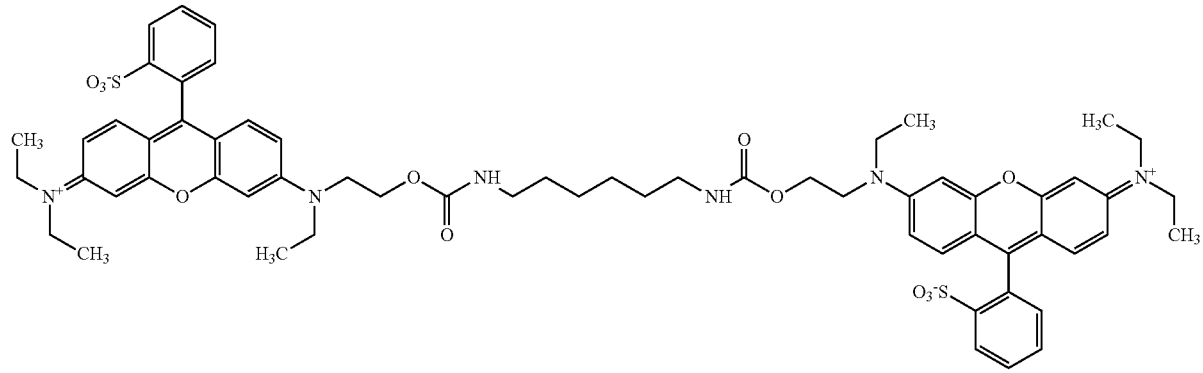
[Chemical Formula 10]
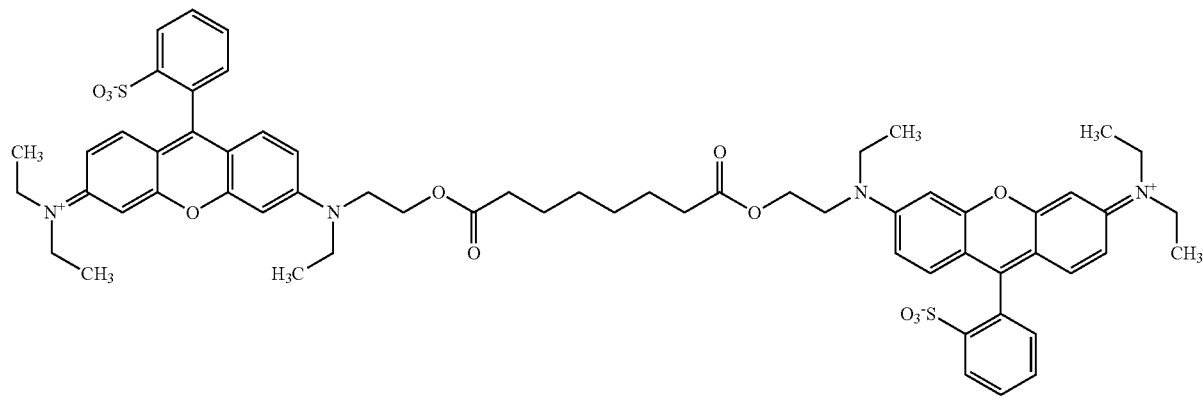
[Chemical Formula 11]
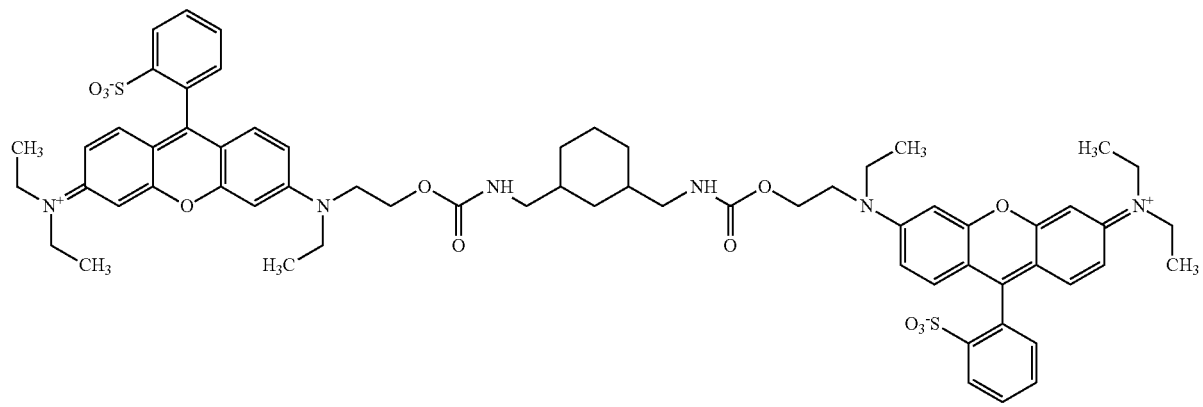

[Chemical Formula 12]
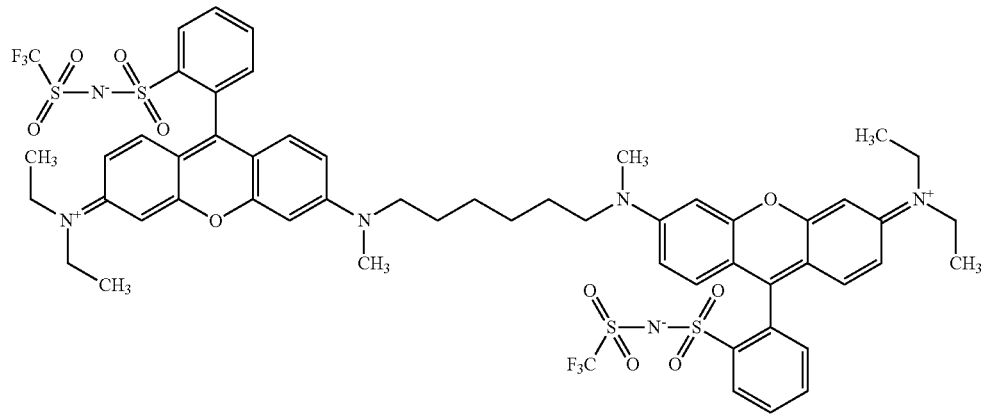
[Chemical Formula 13]
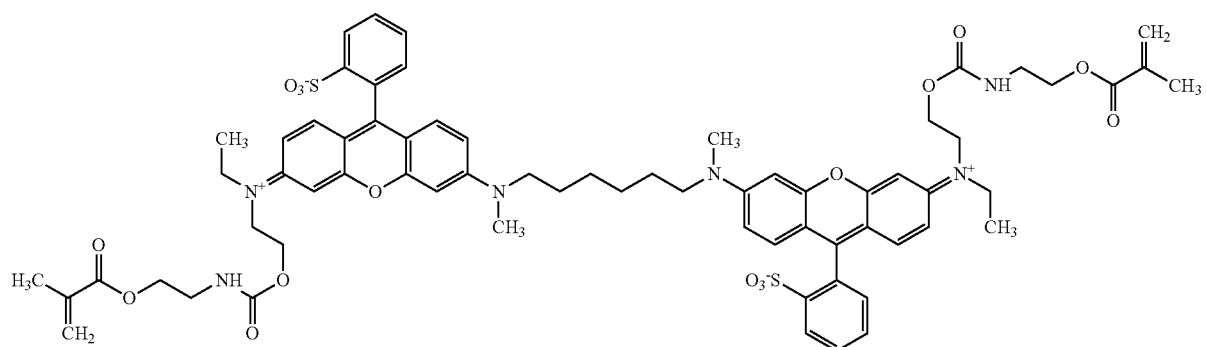
[Chemical Formula 14]
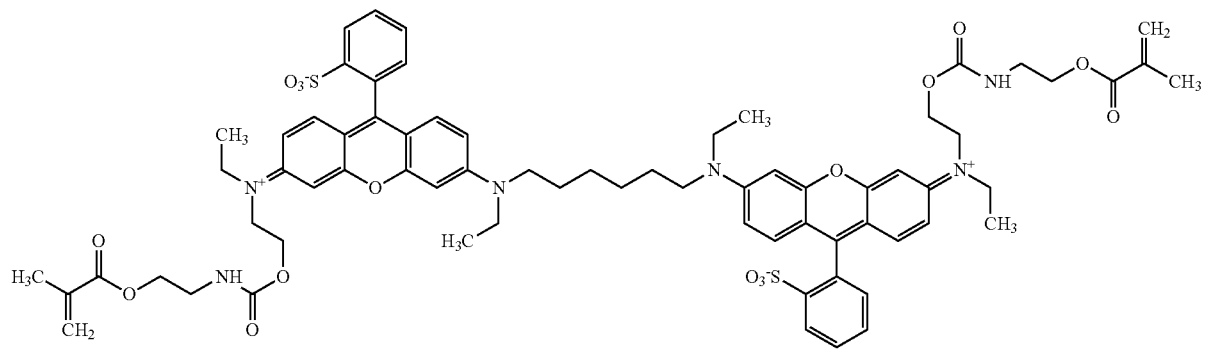
[Chemical Formula 15]
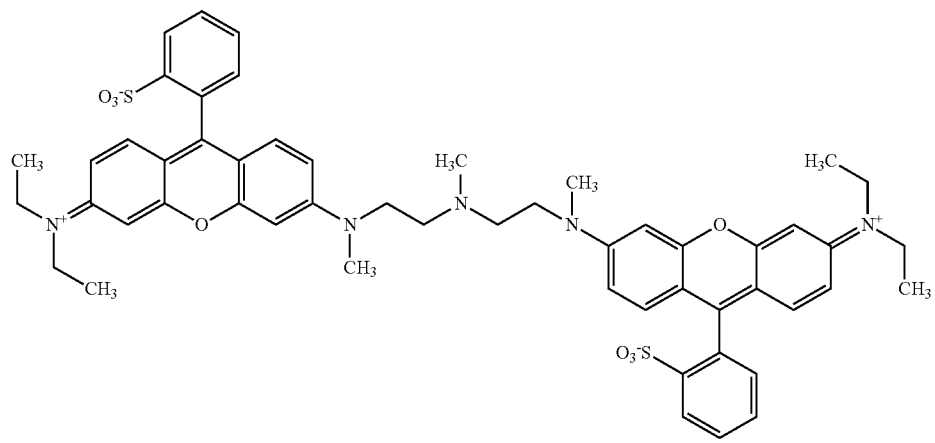

[Chemical Formula 16]
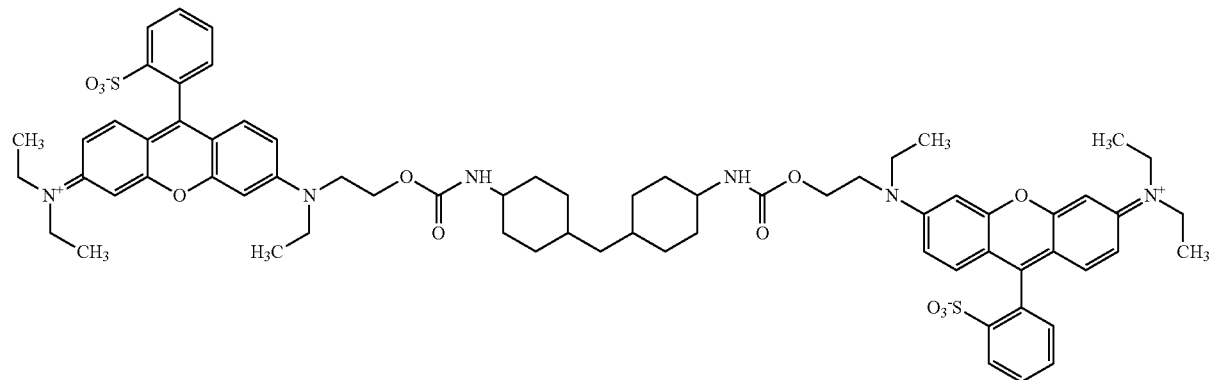
[Chemical Formula 17]
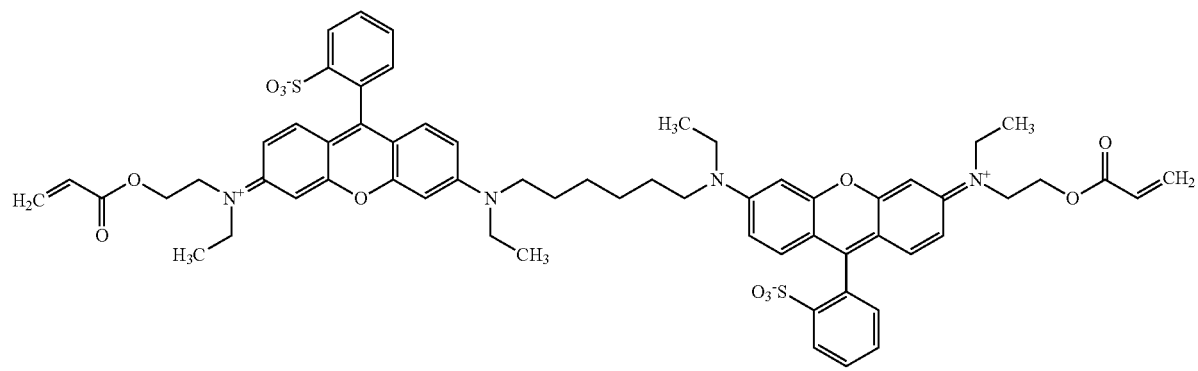
[Chemical Formula 18]
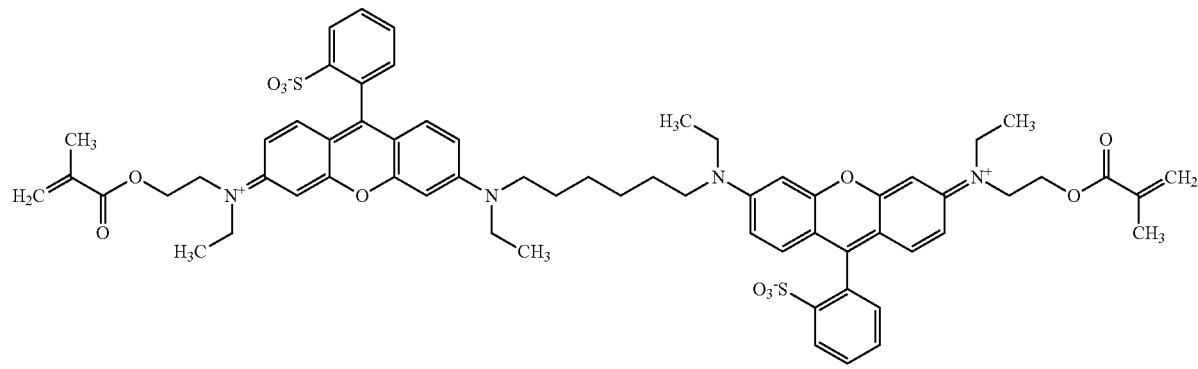
[Chemical Formula 19]
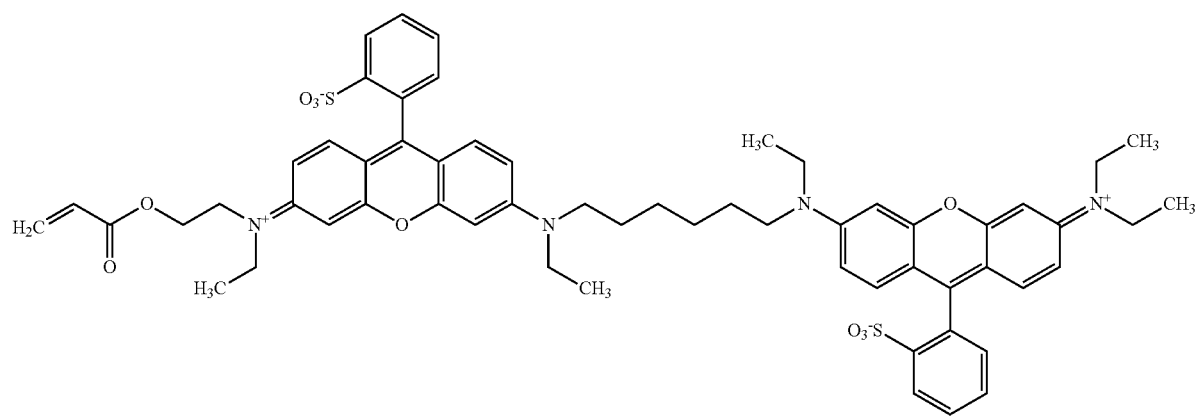

[Chemical Formula 20]

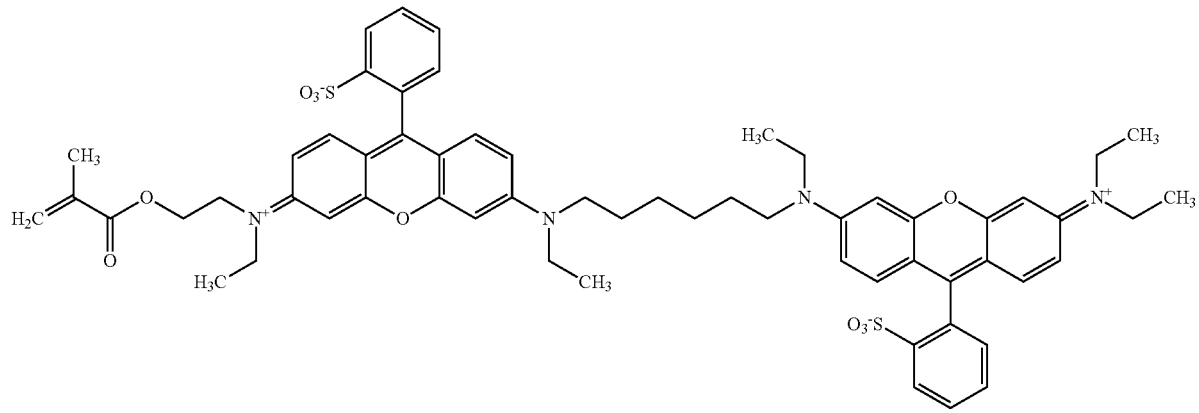

[Chemical Formula 21]

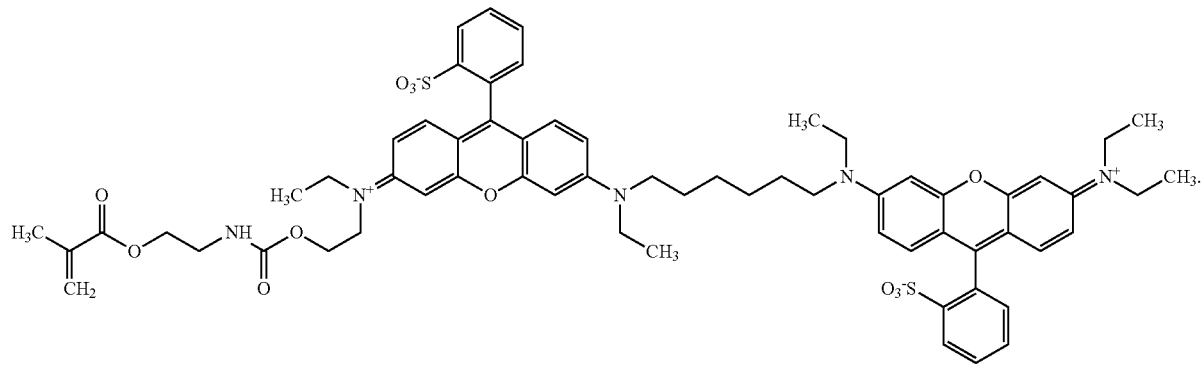

10. The compound as claimed in claim 1, wherein the compound represented by Chemical Formula 1 has a maximum absorbance in a wavelength range of about 500 nm to about 600 nm.

11. A photosensitive resin composition comprising the compound as claimed in claim 1.

12. The photosensitive resin composition as claimed in claim 11, wherein the compound is included in an amount of about 5 wt % to about 10 wt %, based on a total weight of the photosensitive resin composition.

13. The photosensitive resin composition as claimed in claim 11, wherein the compound is a red dye or a blue dye.

14. The photosensitive resin composition as claimed in claim 11, wherein the photosensitive resin composition further includes a binder resin, a photopolymerizable compound, a photopolymerization initiator, and a solvent.

15. The photosensitive resin composition as claimed in claim 14, wherein the binder resin includes an acryl binder resin, a cardo binder resin, or a combination thereof.

16. The photosensitive resin composition as claimed in claim 14, wherein the photosensitive resin composition further includes a pigment along with the compound as a colorant.

17. The photosensitive resin composition as claimed in claim 16, wherein the photosensitive resin composition includes:

about 1 wt % to about 10 wt % of the binder resin;

about 5 wt % to about 60 wt % of the colorant;

about 1 wt % to about 10 wt % of the photopolymerizable compound;

about 0.01 wt % to about 5 wt % of the photopolymerization initiator; and the solvent, all wt % being based on a total weight of the photosensitive resin composition.

18. The photosensitive resin composition as claimed in claim 14, wherein the photosensitive resin composition further includes malonic acid, 3-amino-1,2-propanediol, a silane-based coupling agent including a vinyl group or a (meth)acryloxy group, a leveling agent, a surfactant, a radical polymerization initiator, or a combination thereof.

19. A color filter manufactured using the photosensitive resin composition as claimed in claim 11.

20. A compound represented by Chemical Formula 1:

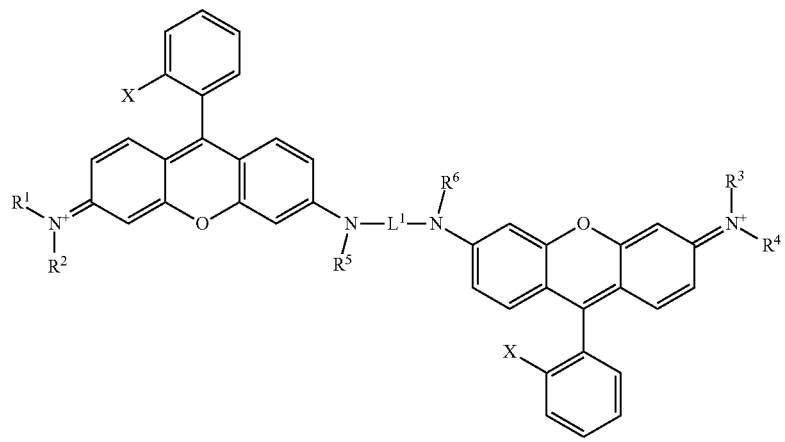

[Chemical Formula 1]

wherein, in Chemical Formula 1,
$R^1$ to $R^6$ are each independently a hydrogen atom, a substituted or unsubstituted C1 to C20 alkyl group, or a substituted or unsubstituted C6 to C20 aryl group,
X is a group represented by Chemical Formula X-1 or Chemical Formula X-2,

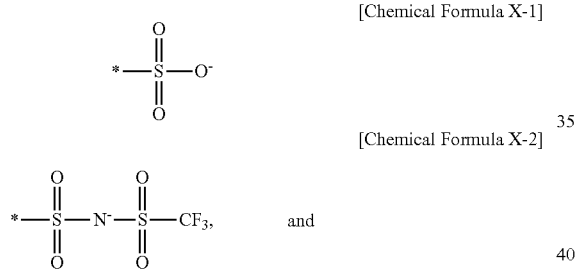

[Chemical Formula X-1]

[Chemical Formula X-2]

and $L^1$ is a group represented by Chemical Formula 3, Chemical Formula 4, or Chemical Formula 5:

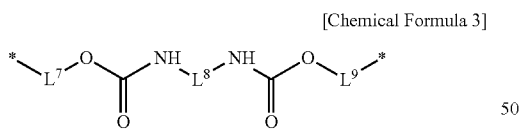

[Chemical Formula 3]

wherein, in Chemical Formula 3, $L^7$ to $L^9$ are each independently a substituted or unsubstituted C1 to C10 alkylene group, a substituted or unsubstituted C3 to C10 cycloalkylene group, or a combination thereof,

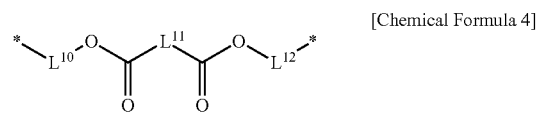

[Chemical Formula 4]

wherein, in Chemical Formula 4, $L^{10}$ to $L^{12}$ are each independently a substituted or unsubstituted C1 to C10 alkylene group, and

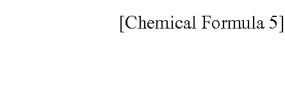

[Chemical Formula 5]

wherein, in Chemical Formula 5,
$L^{13}$ and $L^{14}$ are each independently a substituted or unsubstituted C1 to C10 alkylene group, and
$R^x$ is a substituted or unsubstituted C1 to C10 alkyl group.

* * * * *